(12) United States Patent
Boivin et al.

(10) Patent No.: US 8,791,299 B2
(45) Date of Patent: Jul. 29, 2014

(54) COMPOUNDS FOR THE INHIBITION OF HERPES VIRUSES

(75) Inventors: Guy Boivin, Quebec (CA);
Sheng-Xiang Lin, Quebec (CA);
Melanie Martin, Quebec (CA); Arezki Azzi, Quebec (CA)

(73) Assignee: Universite Laval, Quebec (CA)

( * ) Notice: Subject to any disclaimer, the term of this patent is extended or adjusted under 35 U.S.C. 154(b) by 197 days.

(21) Appl. No.: 13/321,377

(22) PCT Filed: May 19, 2010

(86) PCT No.: PCT/CA2010/000762
§ 371 (c)(1),
(2), (4) Date: Mar. 8, 2012

(87) PCT Pub. No.: WO2010/132992
PCT Pub. Date: Nov. 25, 2010

(65) Prior Publication Data
US 2012/0157538 A1   Jun. 21, 2012

Related U.S. Application Data

(60) Provisional application No. 61/213,240, filed on May 20, 2009.

(51) Int. Cl.
*C07C 243/12* (2006.01)
*C07C 251/18* (2006.01)
*A61K 31/16* (2006.01)
*C07D 239/42* (2006.01)
*C07D 213/40* (2006.01)
*A61K 31/155* (2006.01)

(52) U.S. Cl.
USPC ........... 564/150; 564/148; 564/149; 546/332; 544/242; 514/256; 514/357; 514/615

(58) Field of Classification Search
USPC ........... 564/148, 149, 150; 546/332; 514/357, 514/615, 256; 544/242
See application file for complete search history.

(56) References Cited

U.S. PATENT DOCUMENTS

2009/0233845 A1 * 9/2009 Ray et al. .......... 514/8

FOREIGN PATENT DOCUMENTS

WO   WO-2009088975   7/2009

OTHER PUBLICATIONS

Patent Cooperation Treaty (PCT) International Search Report for International Application No. PCT/CA2010/000762 mailed on Aug. 19, 2010.
Patent Cooperation Treaty (PCT) International Preliminary Report on Patentability for International Application No. PCT/CA2010/000762 mailed on Sep. 9, 2011.
Written Opinion of the International Searching Authority for International Application No. PCT/CA2010/00762 mailed on Aug. 19, 2010.
Written Opinion of the International Preliminary Examining Authority for International Application No. PCT/CA2010/000762 mailed on May 5, 2011.
Answer Summary referring to Documents D1 to D39 as listed on the Written Opinion for PCT/CA2010/000762 dated Jul. 27, 2010.

* cited by examiner

*Primary Examiner* — Shailendra Kumar
(74) *Attorney, Agent, or Firm* — Goodwin Procter LLP

(57) ABSTRACT

3D protein modeling and virtual screening of commercially-available compounds were performed to identify new inhibitors of the herpesvirus DNA polymerase, a key enzyme in the viral replication cycle. Two compounds (Nos 2 and 9) were particularly active against HSV-1 and HSV-2 strains and one compound (No 3) inhibited specifically cytomegalovirus (CMV) strains (overall hit rate of 25%). Some of the tested compounds inhibited wild-type viruses and strains resistant to current antiviral agents. New chemical entity derivatives of compound 2 with binding potential to the DNA polymerase retained an excellent activity against HSV-1, HSV-2 and VZV like the parental compound, as well against strains resistant to current antiviral agents. These non-nucleosidic herpesvirus DNA polymerase inhibitors with in vitro activity against drug-resistant clinical isolates warrant further pre-clinical studies.

28 Claims, 17 Drawing Sheets

Figure 2

| # | Compound name | Catalogue number/supplier |
|---|---|---|
| 1 | N-(2-(2-(2-HYDROXY-5-METHOXYBENZYLIDENE) HYDRAZINO)-2-OXOETHYL)-3-METHYL-BENZAMIDE | R981133/Sigma |
| 2 | N-(2-(2-(2-HYDROXYBENZYLIDENE) HYDRAZINO)-2-OXOETHYL)-1-NAPHTHAMIDE | R122629/Sigma |
| 3 | N-(2-(2-(3-ALLYL-2-HYDROXYBENZYLIDENE)HYDRAZINO)-2-OXOETHYL)-3-CHLOROBENZAMIDE | R941719/Sigma |
| 4 | N-[2-(4-METHOXYPHENYL)ETHYL]-2-[(1-PHENYL-1H-TETRAZOL-5-YL)THIO]ACETAMIDE | 7213912/ChemBridge |
| 5 | 1-(2-CHLORO-5-NITROPHENYLIMINOMETHYL)-2-NAPHTHOL | S698814/Sigma |
| 6 | N-1H-TETRAZOL-5-YL-4-BIPHENYLCARBOXAMIDE | 7246306/Chembridge |
| 7 | 9-ANTHRACENECARBALDEHYDE 1H-TETRAZOL-5-YLHYDRAZONE | 5482924/ChemBridge |
| 8 | N-{[(2-METHYL-2H-TETRAZOL-5-YL) AMINO]CARBONOTHIOYL} -2-THIOPHENECARBOXAMIDE | 7726183/ChemBridge |
| 9 | N-(2-(2-(2-HYDROXY-5-METHOXYBENZYLIDENE) HYDRAZINO)-2-OXOETHYL)-1-NAPHTHAMIDE | R124397/Sigma |
| 10 | N-(2-(2-(3-ALLYL-2-HYDROXYBENZYLIDENE)HYDRAZINO)-2-OXOETHYL)-2-CHLOROBENZAMIDE | R123803/Sigma |
| 11 | N-(2-(2-(3-ALLYL-2-HYDROXYBENZYLIDENE)HYDRAZINO)-2-OXOETHYL)-4-CHLOROBENZAMIDE | R115428/Sigma |
| 12 | N-(2-(2-(3-ALLYL-2-HYDROXYBENZYLIDENE) HYDRAZINO)-2-OXOETHYL)-1-NAPHTHAMIDE | R122726/Sigma |

Figure 4B

C2. (E)-N-(2-(2-(2-hydroxybenzylidene)hydrazinyl)-2-oxoethyl)-1-naphthamide.

C2.01 (E)-N-(2-(2-(3-hydroxybenzylidene)hydrazinyl)-2-oxoethyl)-1-naphthamide

C2,02 (E)-N-(2-(2-(4-hydroxybenzylidene)hydrazinyl)-2-oxoethyl)-1-naphthamide

C2.03 (E)-N-(2-(2-(3,4-dihydroxybenzylidene)hydrazinyl)-2-oxoethyl)-1-naphthamide C2.04 (E)-N-(2-(2-(2,4-dihydroxybenzylidene)hydrazinyl)-2-oxoethyl)-1-naphthamide C2.05 (E)-N-(2-(2-(2,6-dihydroxybenzylidene)hydrazinyl)-2-oxoethyl)-1-naphthamide C2.06 (E)-N-(2-oxo-2-(2-(pyrimidin-4-ylmethylene)hydrazinyl)ethyl)-1-naphthamide C2.07 (E)-N-(2-oxo-2-(2-(pyridin-2-ylmethylene)hydrazinyl)ethyl)-1-naphthamide C2.08 (E)-N-(2-oxo-2-(2-(pyridin-4-ylmethylene)hydrazinyl)ethyl)-1-naphthamide C2.09 (E)-N-(2-oxo-2-(2-(pyridin-3-ylmethylene)hydrazinyl)ethyl)-1-naphthamide C2.10 (E)-N-(2-oxo-2-(2-(pyrimidin-2-ylmethylene)hydrazinyl)ethyl)-1-naphthamide C2.11 (E)-N-(2-(2-((3-hydroxypyridin-2-yl)methylene)hydrazinyl)-2-oxoethyl)-1-naphthamide C2.12 (E)-N-(2-(2-((3-hydroxypyridin-4-yl)methylene)hydrazinyl)-2-oxoethyl)-1-naphthamide C2.13 (E)-N-(2-(2-((2-hydroxypyridin-3-yl)methylene)hydrazinyl)-2-oxoethyl)-1-naphthamide C2.14 (E)-N-(2-(2-(2-aminobenzylidene)hydrazinyl)-2-oxoethyl)-1-naphthamide C2.15 (E)-N-(2-(2-(3-aminobenzylidene)hydrazinyl)-2-oxoethyl)-1-naphthamide C2.16 (E)-N-(2-(2-(4-aminobenzylidene)hydrazinyl)-2-oxoethyl)-1-naphthamide C2.17 (E)-N-(2-(2-(2-fluorobenzylidene)hydrazinyl)-2-oxoethyl)-1-naphthamide C2.18 (E)-N-(2-(2-(3-fluorobenzylidene)hydrazinyl)-2-oxoethyl)-1-naphthamide C2.19 (E)-N-(2-(2-(4-fluorobenzylidene)hydrazinyl)-2-oxoethyl)-1-naphthamide C2.20 (E)-N-(2-(2-(5-fluoro-2-hydroxybenzylidene)hydrazinyl)-2-oxoethyl)-1-naphthamide.

Figure 4C

| ChemScore | Compound |
|---|---|
| 42.54 | C2.04 |
| 40.86 | C2.11 |
| 40.82 | C2.05 |
| 40.53 | C2.08 |
| 40.27 | C2.10 |
| 40.08 | C2.20 |
| 40.05 | C2 |
| 38.98 | C2.12 |
| 38.53 | C2.13 |
| 37.71 | C2.01 |
| 36.98 | C2.16 |
| 36.71 | C2.09 |
| 36.07 | C2.17 |
| 35.82 | C2.06 |
| 35.65 | C2.14 |
| 34.24 | C2.07 |
| 33.33 | C2.15 |
| 32.32 | C2.18 |
| 30.53 | C2.19 |
| 30.52 | C2.03 |
| 26.99 | C2.02 |

Figure 5
Compound 2 derivatives
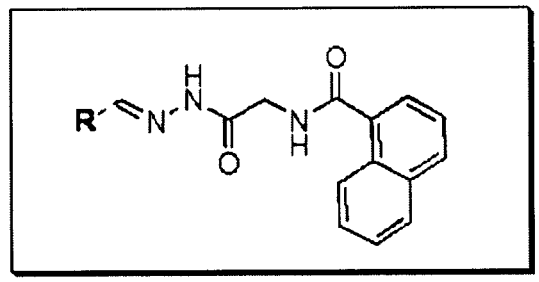
R =
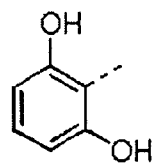
C2.5
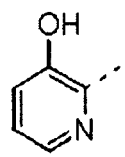
C2.11
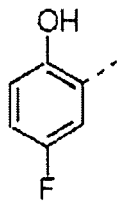
C2.20
Compound 3 derivatives
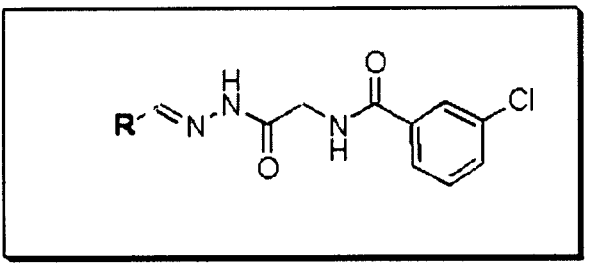
R =
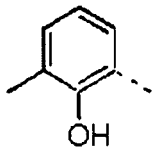
C3-1
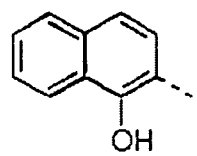
C3-2

Figure 6
A
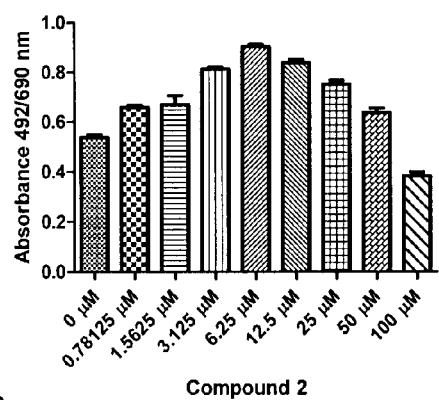 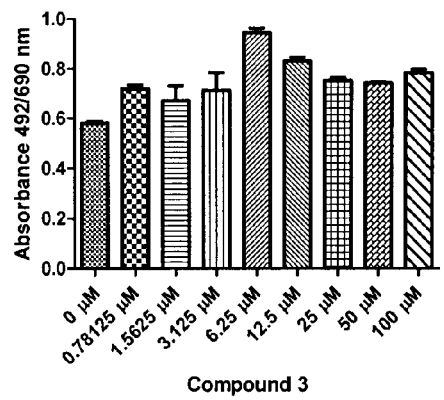
B
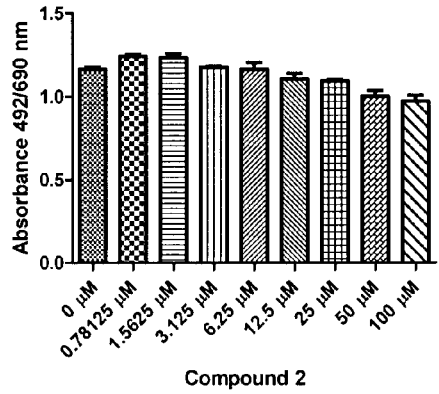 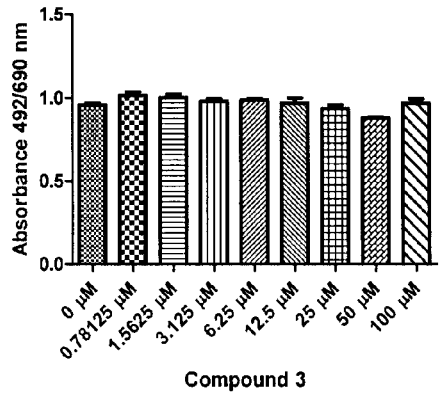

Figure 7A
HSV-1
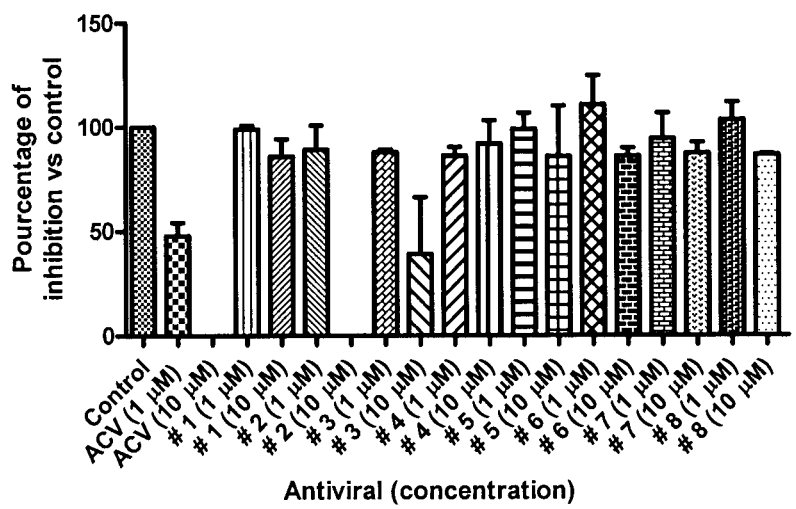
HSV-2
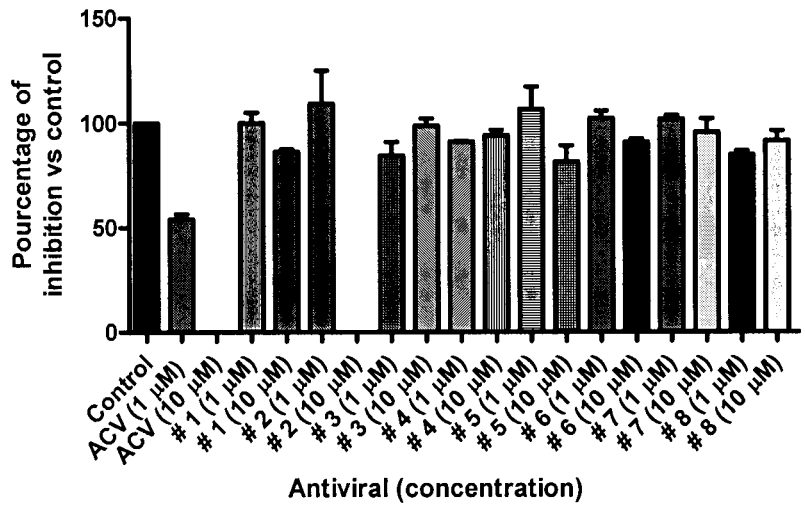

Figure 7B
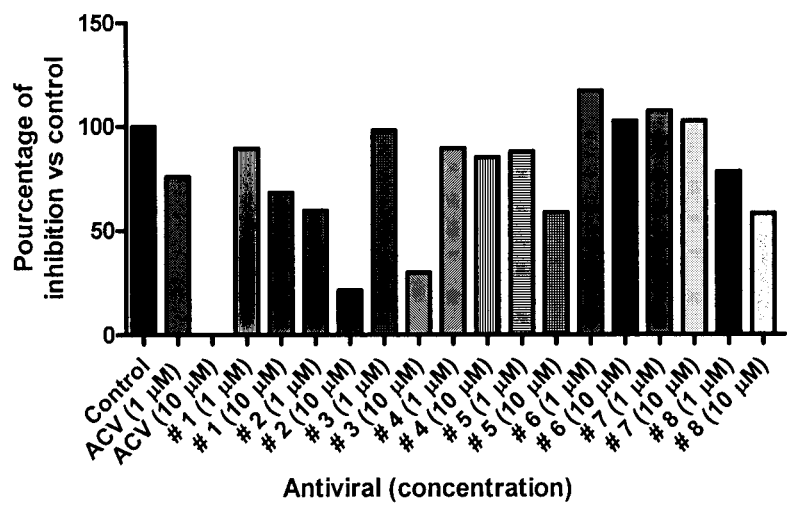
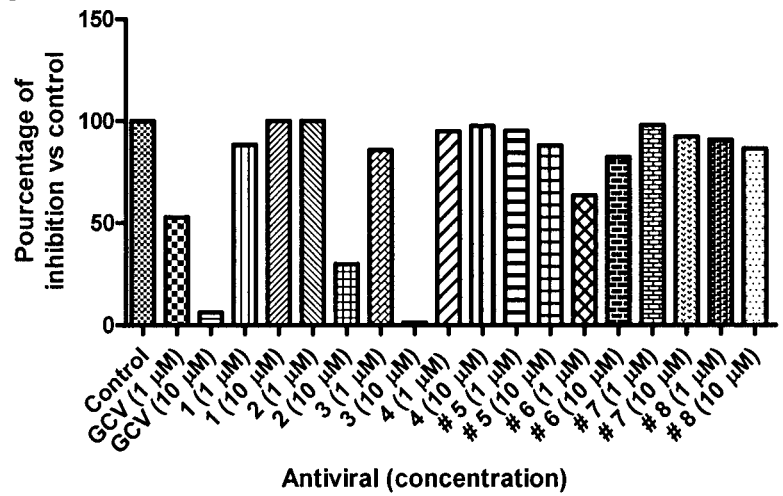

Figure 8

| Viral strains | 50% inhibitory concentration (IC$_{50}$) values (μM) | | | | | |
|---|---|---|---|---|---|---|
| | ACV | GCV | FOS | Compound 2 | Compound 3 | Compound 9 |
| HSV-1 (H25) | 1.2 ± 0.2 | nd | 38,9 | 4.2 ± 0.5 | 9.3 ± 0.8 | 4.2 ± 0.5 |
| HSV-2 (HSV22) | 1.5 ± 0.3 | nd | 83,3 | 4.5 ± 0.6 | 8.2 ± 0.7 | 6.6 ± 0.2 |
| VZV (Ellen) | 4.8 | nd | nd | 9.6 ± 1.6 | 8.8 ± 1.6 | nd |
| CMV (AD169) | nd | 1.6 ± 0.2 | 27.8 ± 0.7 | > 16 | 4.1 ± 1.6 | > 16 |

Abbreviations: ACV, acyclovir; GCV, ganciclovir; FOS, foscarnet; nd, not determined.

Figure 9

| HSV-1 strains | 50% inhibitory concentration (IC$_{50}$) values (μM) | | |
|---|---|---|---|
| | ACV (Fold)* | FOS (Fold)* | Compound 2 (Fold)* |
| H25 (WT) | 1.22 (1) | 38.9 (1) | 4.24 ± 0.48 (1) |
| KOS | 0.4 (0.3) | 44.06 (1.1) | 4.05 ± 0.22 (1) |
| C119629 | 0.42 (0.3) | 14.89 (0.4) | 4.39 ± 0.26 (1) |
| C114093 (ACV-Res)[a] | 17.74 (14.5) | 27.22 (0.7) | 4.72 ± 1.20 (1.1) |
| C80249 (ACV-Res)[b] | 8.51 (7.0) | 28.95 (0.7) | 3.09 ± 0.45 (0.7) |
| L-920062 (FOS-Res)[c] | 1.5 (1.2) | 390.4 (10.0) | 3.49 ± 0.65 (0.8) |

* Fold change compared to the HSV-1 strain H25 (wild-type).

Abbreviations: ACV, acyclovir; FOS, foscarnet; Res, resistant.

[a], The ACV-resistant C114093 carries a truncated version of the thymidine kinase (stop codon leading to a truncated protein of 281 amino acids)

[b], The ACV-resistant C80249 carries a truncated version of the thymidine kinase (stop codon leading to a truncated protein of 225 amino acids) and a DNA polymerase mutation (E756Q)

[c], The FOS-resistant L-920062 carries two DNA polymerase mutations (S724N and P920S)

Figure 10

| HSV-2 strains | 50% inhibitory concentration (IC$_{50}$) values (µM) | | |
|---|---|---|---|
| | ACV (Fold)* | FOS (Fold)* | Compound 2 (Fold)* |
| HSV22 (WT) | 1.51 (1) | 83.3 (1) | 4.52 ± 0.63 (1) |
| MS2 | 3.22 (2.1) | 89.55 (1.1) | 6.62 ± 0.68 (1.5) |
| C75134 | 1.65 (1.1) | 42.86 (0.5) | 6.33 ± 0.39 (1.4) |
| W-940012 (ACV-Res)[a] | 27.01 (17.9) | 91.1 (1.1) | 7.03 ± 0.52 (1.6) |
| C72984 (ACV-Res)[b] | 27.54 (18.2) | 36.88 (0.4) | 6.09 ± 1.08 (1.4) |
| D-900180 (FOS-Res)[c] | 1.99 (1.32) | 367.1 (4.4) | 4.97 ± 0.30 (1.1) |
| M-890546 (ACV/FOS-Res)[d] | 10.73 (7.1) | 234 (2.8) | 7.9 ± 0.57 (1.7) |
| P-920056 (ACV/FOS-Res)[e] | 276.1 (182.8) | 521.1 (6.2) | 5.63 ± 1.31 (1.3) |

* Fold change compared to the HSV-2 strain HSV22 (wild-type).

Abbreviations: ACV, acyclovir; FOS, foscarnet; Res, resistant.

[a], The ACV-resistant W-940012 carries a truncated version of the thymidine kinase (stop codon leading to a truncated protein of 228 amino acids)

[b], The ACV-resistant C72984 carries three mutations in the thymidine kinase (R272V, P273S and N274R)

[c], The FOS-resistant D-900180 carries a DNA polymerase mutation (L850I)

[d], The ACV/FOS-resistant M-890546 carries a DNA polymerase mutation (S729N)

[e], The ACV/FOS-resistant P-920056 carries a truncated version of the thymidine kinase (stop codon leading to a truncated protein of 184 amino acids) and a DNA polymerase mutation (D912V)

Figure 11

| VZV strains | 50% inhibitory concentration (IC$_{50}$) values (µM) | | |
|---|---|---|---|
| | ACV (Fold)* | FOS | Compound 2 (Fold)* |
| Ellen (WT) | 4.8 (1) | nd | 9.6 ± 1.6 (1) |
| GB2000VZV (ACV-Res)[a] | 41 (8.5) | 86.7 | 6.0 ± 2.2 (0.6) |

*, Fold-change compared to the VZV strain Ellen (wild-type)

Abbreviations: ACV, acyclovir; FOS, foscarnet; Res, resistant; nd, not determined

[a.] The ACV-resistant GB2000VZV carries a thymidine kinase mutation (C138R)

Figure 12

| CMV strains | 50% inhibitory concentration (IC$_{50}$) values (µM) | | |
|---|---|---|---|
| | GCV (Fold)* | FOS (Fold)* | Compound 3 (Fold)* |
| AD169 (WT) | 1.61 ± 0.23 (1) | 27.79 ± 0.68 (1) | 4.06 ± 1.61 (1) |
| VQA3 (GCV/FOS-Res)[a] | 27.48 (17.1) | 335.8 (12.1) | 6.12 ± 1.52 (1.5) |
| Xbaf (GCV-Res)[b] | 6.10 (3.8) | 21.29 (0.8) | 8.1 ± 0.70 (2) |

* Fold change compared to the CMV strain AD169 (wild-type).

Abbreviations: GCV, ganciclovir; FOS, foscarnet; Res, resistant.

[a], The GCV/FOS-resistant VQA3 carries two mutations in the DNA polymerase (UL54; F412C and L802M) and one mutation in the UL97 gene (C603W)

[b], The GCV-resistant Xbaf has amino acid deletions at positions 590-593

Figure 13

| | Permeability coefficient ($10^{-6}$ cm/s) ($P_{app}$) |
|---|---|
| Compound 2 | 11,4 |
| Compound 3 | 3,4 |

Figure 14

| Compound ID | Microsomal $Cl_{int}$ (ml/min/mg microsomal protein) | Half-life $t_{1/2}$ (min) | $Cl_{int}$ extrapolated to the whole liver (ml/min/kg protein) |
|---|---|---|---|
| Compound 2 | 0.02105 | 32.93 | 37.26 |
| Compound 3 | 0.0318 | 21.94 | 61.92 |
| Reserpine | 0.0163 | 42.59 | 28.08 |

Figure 15

| Viral strains | 50% inhibitory concentration ($IC_{50}$) values (µM) | | | | |
|---|---|---|---|---|---|
| | C2.05 | C2.11 | C2.20 | C3-1 | C3-2 |
| HSV-1 (H25) | > 16 | > 16 | 8.27 ± 1.70 | > 16 | > 16 |
| HSV-2 (HSV22) | 9.85 ± 3.60 | 8.60 ± 3.50 | 6.50 ± 2.80 | > 16 | > 16 |
| VZV (GB2000VZV) | > 16 | 11.70 ± 2.50 | 5.00 ± 0.80 | > 16 | > 16 |
| CMV (AD169) | > 16 | > 16 | > 16 | > 16 | > 16 |

Figure 16

| Compounds | 50% cytotoxicity (CC$_{50}$) values (μM) | |
|---|---|---|
| | Vero cells | HFFs |
| C2 | 82.1 | 56.2 |
| C2.05 | > 100 | 67.1 |
| C2.11 | > 100 | 52.4 |
| C2.20 | 79.5 | 43.3 |
| C3 | 53.1 | 27 |
| C3-1 | 76.6 | 28.5 |
| C3-2 | 49.1 | 27.2 |
| ACV | > 100 | --- |
| GCV | --- | > 100 |
| FOS | > 100 | > 100 |

Abbreviations: HFFs, human foreskin fibroblasts; ACV, acyclovir; GCV, ganciclovir; FOS, foscarnet

*Reagents and conditions:* (a) methyl glycinate, triethylamine, THF, rt; (b) Hydrazine, MeOH, t.p; (c) corresponding aldehyde (C2.11: 3-hydroxypyridine-2-carboxaldehyde; C2.5: 2,6 dihydroxybenzaldehyde; C2.20: 5-Fluoro-2-hydroxybenzaldehyde); compound 2 : 2-hydroxybenzaldehyde), EtOH, rt.

*Reagents and conditions:* (a) methyl glycinate, triethylamine, THF, rt; (b) Hydrazine, MeOH, t.p; (c) corresponding
aldehyde (C3-1: 2-hydroxy-3-methylbenzaldehyde; C3-2: 1-Hydroxy-2-naphtaldehyde; Compound 3: 2-hydroxy-3-(prop-2-en-1-yl)benzaldehyde), EtOH, rt.

COMPOUNDS FOR THE INHIBITION OF
HERPES VIRUSES

RELATED APPLICATIONS

This application is a national stage filing under 35 U.S.C. 371 of PCT/CA2010/000762, filed May 19, 2010, which claims the benefit of and priority to U.S. Provisional Patent Application No. 61/213,240, filed May 20, 2009.

FIELD OF THE INVENTION

The present invention relates to compounds and their use in impairing the replication of herpesviruses. These compounds are particularly active against the herpes simplex viruses (HSV) types-1 and -2, the cytomegalovirus (CMV) and the varicella-zoster virus (VZV) and may be used to inhibit wild-type viruses or strains resistant to current antiviral agents.

BACKGROUND OF THE INVENTION

Herpesviruses are DNA-containing enveloped viruses belonging to the Herpesviridae family. Among these viruses, HSV-1 and HSV-2 are responsible for recurrent orolabial and genital infections, VZV is responsible for chickenpox and shingles and CMV is associated with disseminated infections such as pneumonitis, colitis and retinitis in immunocompromised individuals. All herpesviruses establish lifelong latent infections in humans with periodic symptomatic and asymptomatic reactivations.

Antiviral agents are commonly used to treat frequent HSV reactivations (mainly genital infections) in immunocompetent individuals, VZV reactivation (shingles or zoster) in elderly subjects and severe HSV, VZV and CMV infections in immunocompromised hosts such as HIV-infected patients, transplant recipients and subjects with neoplasia. Active compounds currently available for the treatment of herpesvirus infections include the nucleoside analogues acyclovir (ACV and its prodrug valacyclovir or VACV), penciclovir (PCV and its prodrug famciclovir), and ganciclovir (GCV and its prodrug valganciclovir or VGCV) as well as the nucleotide analogue cidofovir (CDV) and the pyrophosphate analogue foscarnet (FOS). All these compounds interfere with viral DNA synthesis by inhibiting the viral DNA polymerase (pol). The nucleoside and nucleotide analogues must be phosphorylated to exert their antiviral effect whereas the pyrophosphate analogue FOS directly inhibits viral DNA pol. The nucleoside analogues ACV and GCV are considered the first-line drugs against HSV/VZV and CMV diseases, respectively, whereas CDV and FOS are considered second-line drugs due to their important toxicity (nephrotoxicity and electrolyte imbalances) and lack of oral formulations.

The emergence of herpesvirus drug resistance is frequent in immunocompromised subjects and only surpassed by that of HIV resistance [1]. For instance, HSV resistance to ACV, the first-line drug, varies from 4 to 14% among various immunocompromised groups, although it is infrequent in immunocompetent subjects [1]. The rate of CMV resistance to the gold standard GCV is also substantial with 7% resistance after 6 months of treatment in HIV-infected patients [2] and up to 30% in lung transplant recipients [3]. Due to less frequent use, fewer data on CMV resistance to CDV and FOS have been reported. Some CMV studies reported resistance rate to FOS and CDV similar or higher to that observed with GCV [4,5]. Resistance to the nucleoside analogues can be conferred by alterations in the viral activating gene (HSV/VZV thymidine kinase or CMV UL97 protein kinase) or in the target gene, i.e. the viral DNA pol. Resistance to CDV and FOS arises from mutations in the viral DNA pol gene only. Notably, some mutations in the viral DNA pol gene can confer resistance to all currently-available antiviral agents [6,7]. Thus, there is an urgent need to develop other non-toxic and highly effective compounds with different mechanisms of action to inhibit herpesvirus replication.

The aim of this project was to identify compounds with high binding potential to the DNA pol of HSV-1 by using a strategy that combines 3D modeling and virtual screening of a large bank of compounds. The antiviral activity and toxicity of the top leading compounds were examined in vitro against HSV-1, HSV-2, VZV and CMV. Recombinant and clinical isolates suceptible and/or resistant to current antivirals prescribed for the treatment of herpesvirus infections were used to determine the antiviral potential of these new compounds.

SUMMARY OF THE INVENTION

The present invention relates to compounds, pharmaceutical compositions comprising these compounds and their use in impairing or inhibiting (e.g., interfering) herpesvirus replication. Some of the compounds of the present are readily available to the public while others are new chemical entities.

The present invention especially contemplates compounds that are new chemical entities. However, both new chemical entities and known compounds may be used in pharmaceutical compositions and in methods of inhibiting herpesvirus replication.

Compounds of formula IA and IB that are described herein may be suitable for impairing herpesvirus replication. Some compounds of formula IA have been found particularly suitable for interfering with the replication of herpes simplex 1 and herpes simplex 2 while some compounds of formula IB have been found particularly suitable for interfering with the replication of cytomegaloviruses. Both compounds of formula IA and IB have also the ability to interfere with the replication of varicella zoster virus.

Some of the compounds described herein may even be used to interfere with the replication of herpesviruses that show resistance to other antivirals including, acyclovir, ganciclovir and/or foscarnet.

The invention also provides chemical intermediates of formula $IA^1$, $IA^2$, $IB^1$ and $IB^2$ that may be used in the manufacture of compounds of formula IA or IB.

Methods for identifying a ligand capable of interacting with a herpesvirus DNA polymerase are also encompassed herewith. The method entails using computer-generated models of a putative ligand and of a HSV-1 DNA polymerase pocket that is located near its active site. Putative compounds that fit into the pocket may be selected according to an estimation of the free energy of ligand binding and hydrogen bonding potential of the ligand with the DNA polymerase.

The pocket of interest is delimited by residues Val715, Asp717, Ser720, Arg785, Lys811, Asn815, Tyr884 and Lys939. Selected compounds may be tested for their ability to interfere with the activity of the DNA polymerase (accession No. CAA32323). For example, the putative ligand may be obtained and tested for in vitro inhibition of replication of a herpesvirus using a method described herein. The present invention thus also relates to compounds that are selected by this method and that are capable of inhibiting viral replication.

BRIEF DESCRIPTION OF THE DRAWINGS

In drawings which illustrates non-limitative exemplary embodiments of the present invention.

FIG. 2 is a table representing the high ranking compounds selected from virtual screening of the HSV-1 DNA polymerase active site near $Mg^{2+}$;

FIG. 4B represents the name of compound 2 derivatives;

FIG. 4C is a table representing the result of the docking simulation of chemical compounds derived from compound 2 on HSV-1 DNA polymerase. Docking was done with GOLD v.3.2 software and compounds were ranked with ChemScore function;

FIG. 5 represents the chemical structure of selected derivatives of compounds 2 and 3;

FIG. 6 shows histograms describing the toxicity of the most potent compounds 2 and 3 on Vero (A) and HFF (B) cells using a MTS assay.

FIG. 7A Screening activity of compounds 1 to 8 against representative HSV-1 (A) and HSV-2 (B) strains;

FIG. 7B Screening activity of compounds 1 to 8 against representative VZV (C) and CMV (D) strains;

FIG. 8 is a table representing the $IC_{50}$ values for the most potent compounds 2, 3 and 9 against herpesvirus reference strains;

FIG. 9 is a table representing the antiviral activity of compound 2 against wild-type and drug-resistant HSV-1 clinical isolates and recombinant viruses;

FIG. 10 is a table representing the antiviral activity of compound 2 against wild-type and drug-resistant HSV-2 clinical isolates;

FIG. 11 is a table representing the antiviral activity of compound 2 against a wild-type VZV strain and a drug-resistant VZV clinical isolate;

FIG. 12 is a table representing the antiviral activity of compound 3 against wild-type and drug-resistant CMV clinical isolates;

FIG. 13 is a table representing the results of Parrallel Artificial Membrane Permeability Assays (PAMPA) for compounds 2 and 3;

FIG. 14 is a table representing the results of microsomal stability of compounds 2 and 3 using male rat liver microsomes;

FIG. 15 is a table representing the antiviral activity of compounds 2 and 3 derivatives against herpesvirus strains;

FIG. 16 is a table representing the toxicity of compounds 2 and 3 and their derivatives for Vero cells and HFFs;

DETAILED DESCRIPTION OF THE INVENTION

Figure 1:
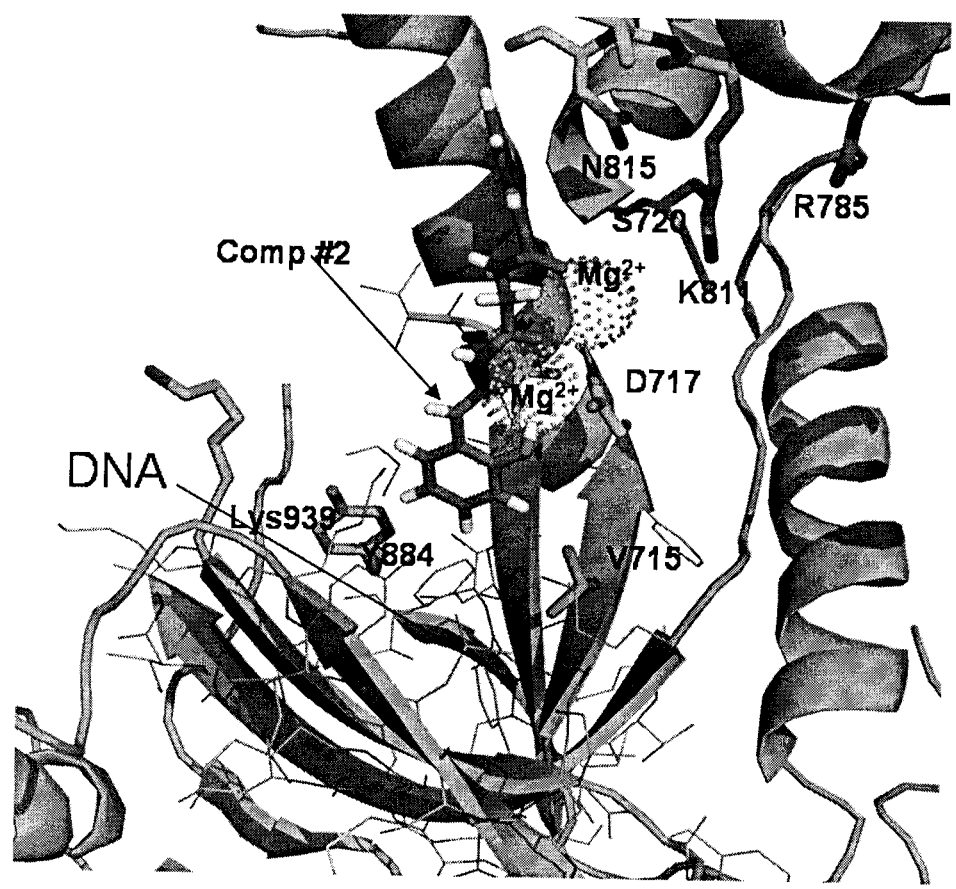
FIG. 1 is a schematic representation of the structure of HSV-1 DNA polymerase docking cleft used in virtual screening experiments delimited by residues Val715, Asp717, Ser720, Arg785, Lys811, Asn815, Tyr884, Lys939.

The present invention relates to compounds, pharmaceutical compositions comprising these compounds and their use in impairing or inhibiting herpesvirus replication. Some of the compounds of the present are readily available to the public while others are new chemical entities.

The present invention especially contemplates compounds that are new chemical entities. However, both new chemical entities and known compounds may be used in pharmaceutical compositions and in methods and uses for inhibiting herpesvirus replication.

In an aspect, the present invention relates to a compound of formula IA or formula IB or a pharmaceutically acceptable salt thereof as well as pharmaceutical compositions comprising such compounds and a pharmaceutically acceptable carrier;

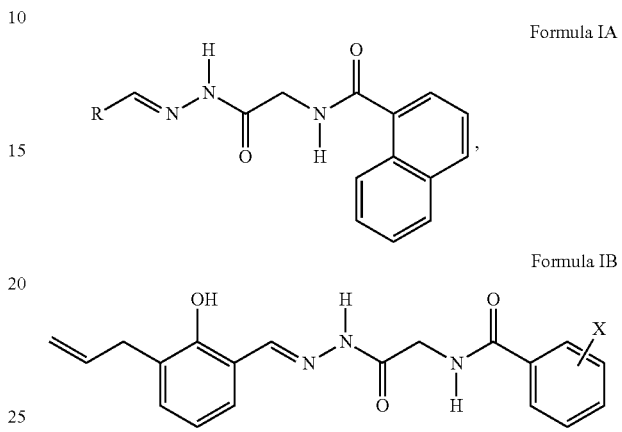

where R may be selected, for example, from the group consisting of:

a) unsubstituted benzyl or a substituted benzyl of formula II b) an unsubstituted pyridine or a substituted pyridine selected from the group consisting of:

and c) a pyrimidine selected from the group consisting of

X and Y may each independently be selected from the group consisting of H, $-OR_1$, $NH_2$, F, Cl, Br, I, an alkyl group of 1 to 3 carbon atoms and an allyl group, and;

$R_1$ may be selected from the group consisting of H and an alkyl group of 1 to 3 carbon atoms.

In accordance with the present invention, the compound may be, for example, a compound of formula IA, wherein R may be selected, for example, from the group consisting of unsubstituted benzyl or a substituted benzyl of formula II:

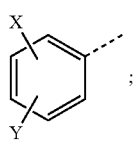

and,
an unsubstituted pyridine or a substituted pyridine of formula:

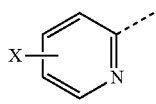

wherein X and Y each may independently be selected from the group consisting of H, —OR$_1$, NH$_2$, F, Cl, Br, I, an alkyl group of 1 to 3 carbon atoms and an allyl group and wherein R$_1$ may be selected from the group consisting of H and an alkyl group of 1 to 3 carbon atoms.

In accordance with an embodiment of the invention R may be a substituted benzyl of formula II, where X may be OR$_1$ and Y may be either F, OR$_1$ or H.

In accordance with a specific embodiment of the invention, X may be OH and Y may be F.

In accordance with another specific embodiment of the invention, X may be OH and Y may be H.

In accordance with yet another specific embodiment of the invention, X may be OR$_1$ and Y may be OH. In such instance R$_1$ may be, for example H or methyl.

Also in accordance with the present invention, the compound may be, for example, a compound of formula IA, where R may be a substituted pyridine of formula

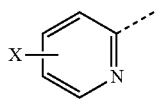

and where X is OR$_1$.

In accordance with a specific embodiment of the invention, R$_1$ may be, for example, H.

In an exemplary embodiment, the compound of the present invention may be selected from those of formula IA, wherein R is a substituted benzyl of formula II:

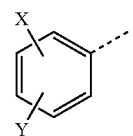

wherein X may be H or OR$_1$ and wherein Y is OH.

In accordance with a specific embodiment of the invention, X may be OR$_1$ while Y may be OH. In accordance with another specific embodiment of the invention, X may be H while Y may be OH. In accordance with yet another exemplary embodiment, X may be OMe while Y may be OH.

In another exemplary embodiment, the compound of the present invention is selected from those of formula IA, wherein R may be for example, a hydroxy-substituted benzyl of formula:

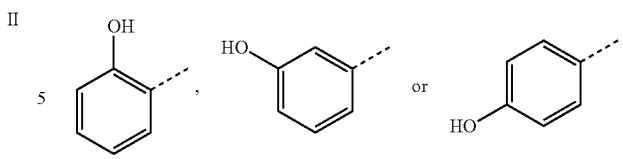

In accordance with a particular embodiment of the invention, R may be for instance, a hydroxy-substituted benzyl of formula:

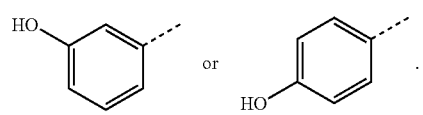

In accordance with another particular embodiment of the invention, R may be for instance a substituted benzyl of formula:

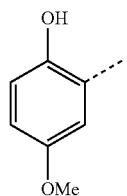

In an exemplary embodiment, the compound of the present invention may be selected from those of formula IA, wherein R is a substituted benzyl of formula II:

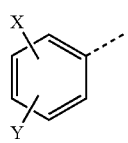

and wherein X and Y are both OH.

In accordance with an exemplary embodiment of the invention R may be a hydroxy-substituted benzyl of formula:

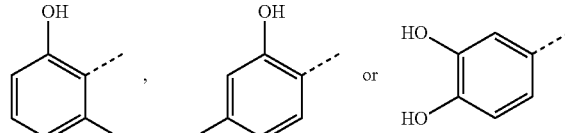

In accordance with a specific embodiment of the invention R may be for example, a hydroxy-substituted benzyl of formula,

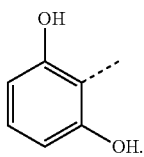

In a further exemplary embodiment, the compound of the present invention may be selected from those of formula IA, wherein R is a substituted benzyl of formula II:

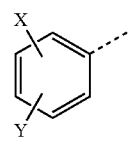

wherein X may be H or OH and wherein Y may be F, Cl, Br or I.

In accordance with a particular embodiment of the invention X may be OH while Y may be F.

In accordance with an exemplary embodiment of the invention R may be, for example a substituted benzyl of formula:

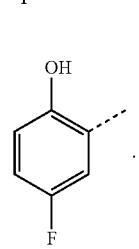

In an additional embodiment, the compound of the present invention may be selected from those of formula IA, wherein R is a substituted pyridine selected from the group consisting of:

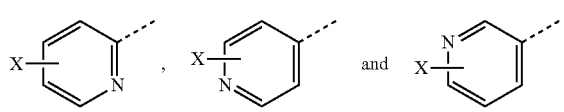

and wherein X is OH.

In an exemplary embodiment of the invention, R may be, for example, a substituted pyridine group of formula:

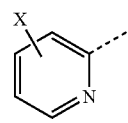

In accordance with the invention, X may be OH. The substituted pyridine group may thus be, for instance:

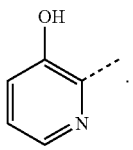

In another exemplary embodiment of the invention, R may be, for example, a substituted or unsubstituted (wherein X is H) pyridine of formula:

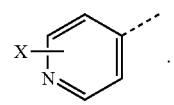

In yet another exemplary embodiment of the invention, R may be, for example, a pyrimidine group of formula:

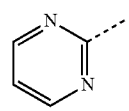

In a further embodiment, the compound of the present invention may be selected from those of formula IB wherein X is of H, —$OR_1$, $NH_2$, F, Cl, Br, I, an alkyl group of 1 to 3 carbon atoms and an allyl group and; wherein $R_1$ is selected from the group consisting of H and an alkyl group of 1 to 3 carbon atoms. In a particular embodiment, X may be, for example, F, Cl, Br or I. In a more specific embodiment X may be Cl.

In accordance with an embodiment of the invention, the compound of formula IB may have the following formula:

In some aspect of the invention including for example, pharmaceutical compositions, uses and methods, the compounds listed below or listed in FIG. 2 may be included, while in other aspects (compounds per se) these compounds may, if desired, be excluded from the invention:

i. N-(2-(2-(2-hydroxybenzylidene)hydrazino)-2-oxoethyl)-1-naphthamide;
  ii. N-(2-(2-(2-hydroxy-5-methoxybenzylidene)hydrazino)-2-oxoethyl)-1-naphthamide, or
  iii. N-(2-(2-(3-allyl-2-hydroxybenzylidene)hydrazino)-2-oxoethyl)-1-naphthamide.

In another aspect the present invention provides a compound of formula IA or a pharmaceutically acceptable salt thereof, Formula IA

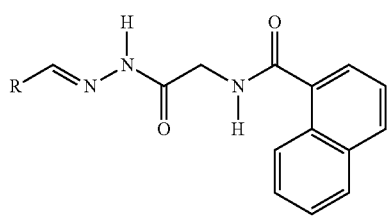

wherein R may be selected, for example, from the group consisting of:

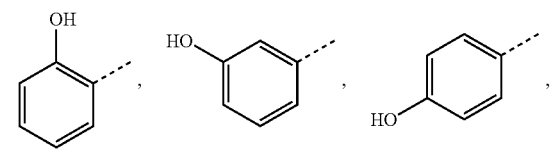

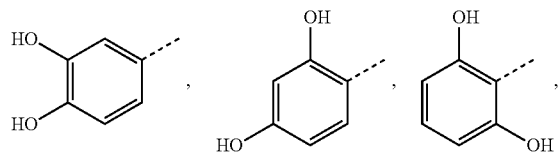

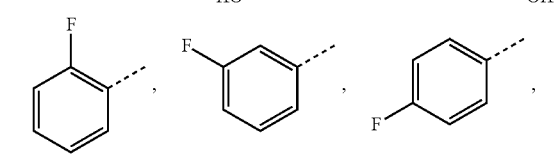

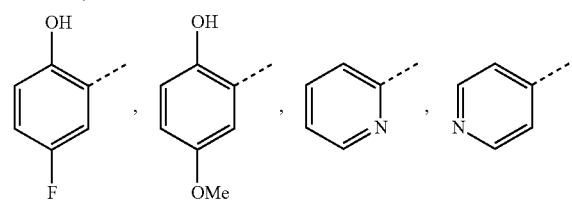

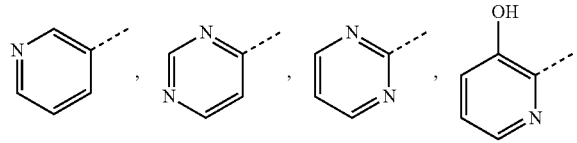

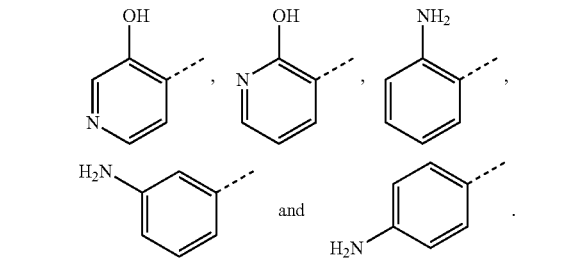

In accordance with an embodiment of the invention, R may be more particularly selected from the group consisting of:

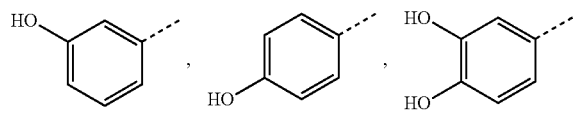

-continued

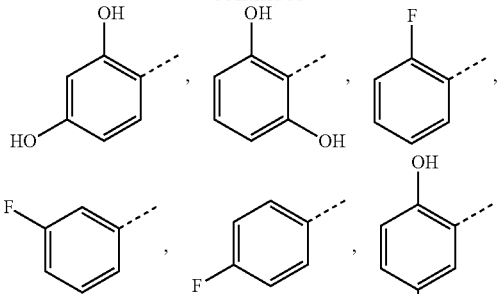

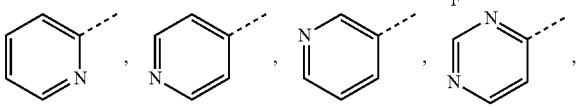

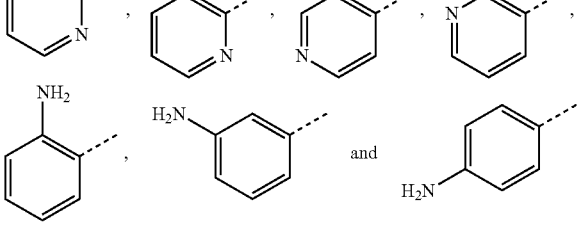

In accordance with a specific embodiment of the invention, R may be more particularly selected from the group consisting of:

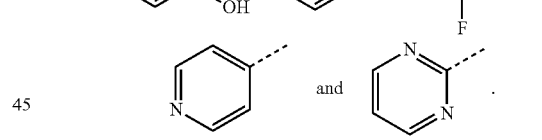

In accordance with another specific embodiment of the invention, R may be more particularly selected from the group consisting of:

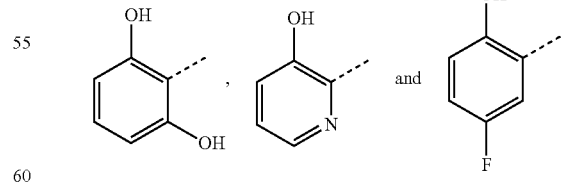

In a further aspect, the present invention relates to the use of the compounds of formula IA and/or formula IB or other compounds as described herein for interfering with (e.g., treating, preventing) a herpesvirus replication. Compounds of the present invention may found particular use in the inhibition of herpesvirus replication, thereby reducing the viral load. The compounds of formula IA and/or IB described herein may be capable of interacting with the DNA polymerase of some herpesviruses and thereby impairing the activity of the DNA polymerase.

Some of the compounds described herein may be suitable for interfering with the replication of herpesvirus such as herpes simplex 1, herpes simplex 2, cytomegalovirus and/or varicella zoster virus.

For instance, some compounds of formula IA or pharmaceutically acceptable salts have a better activity against herpes simplex 1 and/or herpes simplex 2 and may thus be particularly suitable to inhibit the replication of these herpesviruses.

Some compounds of formula IA or their pharmaceutically acceptable salts have also been found suitable for inhibiting the replication of herpesviruses that are characterized as being resistant to a nucleoside analogue and/or a pyrophosphate analogue.

For example, some compounds of formula IA or their pharmaceutically acceptable salts have also been found suitable for inhibiting the replication of herpesviruses that are characterized as being resistant to foscarnet or resistant to a nucleoside analogueacyclovir and/or foscarnet as well as to foscarnet.

Compounds of formula IB or pharmaceutically acceptable salts have a better activity against cytomegalovirus and may thus be particularly suitable to inhibit the replication of this herpesvirus.

It has also been found that some compounds of formula IB or their pharmaceutically acceptable salts may be capable of impairing the replication of viruses that are otherwise resistant to a nucleoside analogue and/or a pyrophosphate analogue.

For example, some compounds of formula IB or their pharmaceutically acceptable salts have been found suitable for inhibiting the replication of herpesviruses that are resistant to ganciclovir and/or foscarnet.

In an additional aspect, the present invention provides a pharmaceutical composition comprising a compound or a pharmaceutically acceptable salt thereof of formula IA or IB or any other compounds described herein and a pharmaceutically acceptable carrier.

Such pharmaceutical composition may be used for interfering with herpesvirus replication. The herpesviruses that are more specifically targeted are for example, herpes simplex 1, herpes simplex 2, cytomegalovirus and varicella-zoster. However, other herpesviruses may be targeted such as herpesvirus type 6, 7 and 8 as well as Epstein Barr virus.

Pharmaceutical composition comprising compounds of formula IA may be suitable for impairing the replication of herpes simplex 1 or herpes simplex 2 as well as varicella-zoster virus. Such pharmaceutical composition may also be suitable for impairing the replication of herpesviruses (e.g., HSV-1, HSV-2, VZV) that are characterized as being resistant to acyclovir and/or foscarnet.

Pharmaceutical composition comprising compounds of formula IB may be suitable for impairing the replication of cytomegalovirus. Such pharmaceutical composition may also be suitable for impairing the replication of cytomegaloviruses that are characterized as being resistant to ganciclovir and/or foscarnet.

In a further aspect, the present invention provides a method of treating or preventing a herpesvirus infection. The method may comprise administering a compound or a pharmaceutically acceptable salt thereof of formula IA or IB or any other compounds described herein to a mammal in need.

In accordance with the invention, the mammal in need may be immunocompetent or may be immunocompromised.

For example, immunocompromised individuals who may benefit from such treatment are those who suffer from HIV-infection or neoplasia or transplant recipients.

The method of the present invention may be particularly useful for treating or preventing infections in mammals which are infected with herpesviruses including those who suffer from chickenpox or shingles associated with varicella-zoster virus, oro-labial or genital infection associated with HSV-1 or HSV-2 or pneumonitis, colitis or retinitis associated with cytomegalovirus.

In accordance with the present invention, the mammal may be infected with or is suffering from an infection caused by herpes simplex 1, herpes simplex 2, cytomegalovirus or varicella-zoster virus.

Methods of treatment of the present invention entail administering, for example, a compound of formula IA or a pharmaceutically acceptable salt to a mammal suffering from an infection with herpes simplex 1 or herpes simplex 2. Methods of treatment with compounds of formula IA may be particularly suitable for treating a mammal having a virus that is resistant to treatment with acyclovir or acyclovir prodrug and/or foscarnet.

Other methods of treatment of the present invention entail administering, for example, a compound of formula IB or a pharmaceutically acceptable salt to a mammal suffering from an infection with cytomegalovirus. Methods of treatment with compounds of formula IB may be particularly suitable for treating a mammal having a virus that is resistant to treatment with ganciclovir or a ganciclovir prodrug and/or foscarnet.

In yet a further aspect, the present invention provides a method for interfering with the replication of a herpesvirus from a cell. The method may comprise contacting a cell infected by the herpesvirus (or susceptible to being infected by the herpesvirus) with a compound of formula IA or IB or a pharmaceutically acceptable salt thereof as defined herein. Again, such method is particularly beneficial for interfering with the replication of herpes simplex 1, herpes simplex 2, cytomegalovirus and varicella zoster virus.

The method may be carried out by contacting a cell infected or susceptible to being infected with herpes simplex 1 or herpes simplex 2, with a compound of formula IA. Such method may be carried out for viruses that are resistant to acyclovir and/or foscarnet.

The method may also be carried out by contacting a cell infected or susceptible to being infected with a cytomegalovirus, with a compound of formula IB. Such method may be carried out for viruses that are resistant to ganciclovir and/or foscarnet.

In yet a further aspect, the present invention provides a method for identifying a ligand capable of interfering with the replication of herpesvirus. The method may comprise docking a computer-generated model of a putative ligand onto a computer-generated model of a pocket located near the active site of a HSV-1 DNA polymerase (in a non-replicating state), and selecting compounds according to an estimation of a ChemScore. Ligands with lowest free binding energy and higher hydrogen bonding potential to the DNA polymerase are selected for in vitro tests.

The pocket is delimited by residues Val715, Asp717, Ser720, Arg785, Lys811, Asn815, Tyr884 and Lys939 and therefore compounds that can fit into this pocket may be identified as putative ligand of the DNA polymerase and may also potentially interfere with the activity of this enzyme.

The putative ligand may be obtained and tested for in vitro inhibition of herpesvirus replication using a method described herein.

Other aspects of the invention relates to a ligand obtained by the method described herein. Such ligand may potentially be used for inhibiting herpesvirus replication.

In another aspect, the present invention relates to a pharmaceutical composition comprising a compound selected, for example, from the group consisting of:

N-(2-(2-(2-hydroxy-5-methoxybenzylidene)hydrazino)-2-oxoethyl)-3-methyl-benzamide;
N-(2-(2-(2-hydroxybenzylidene)hydrazino)-2-oxoethyl)-1-naphthamide;
N-(2-(2-(3-allyl-2-hydroxybenzylidene)hydrazino)-2-v)-3-chlorobenzamide;
N-[2-(4-methoxyphenyl)ethyl]-2-[(1-phenyl-1H-tetrazol-5-yl)thio]acetamide;
1-(2-chloro-5-nitrophenyliminomethyl)-2-naphthol;
N-1H-tetrazol-5-yl-4-biphenylcarboxamide;
9-anthracenecarbaldehyde1H-tetrazol-5-ylhydrazone;
N-{[(2-methyl-2H-tetrazol-5-yl)amino]carbonothioyl}-2-thiophenecarboxamide;
N-(2-(2-(2-hydroxy-5-methoxybenzylidene)hydrazino)-2-oxoethyl)-1-naphthamide;
N-(2-(2-(3-allyl-2-hydroxybenzylidene)hydrazino)-2-oxoethyl)-2-chlorobenzamide;
N-(2-(2-(3-allyl-2-hydroxybenzylidene)hydrazino)-2-oxoethyl)-4-chlorobenzamide;
N-(2-(2-(3-allyl-2-hydroxybenzylidene)hydrazino)-2-oxoethyl)-1-naphthamide;
(E)-N-(2-(2-(2-hydroxybenzylidene)hydrazinyl)-2-oxoethyl)-1-naphthamide;
(E)-N-(2-(2-(3-hydroxybenzylidene)hydrazinyl)-2-oxoethyl)-1-naphthamide;
(E)-N-(2-(2-(4-hydroxybenzylidene)hydrazinyl)-2-oxoethyl)-1-naphthamide;
(E)-N-(2-(2-(3,4-dihydroxybenzylidene)hydrazinyl)-2-oxoethyl)-1-naphthamide;
(E)-N-(2-(2-(2,4-dihydroxybenzylidene)hydrazinyl)-2-oxoethyl)-1-naphthamide;
(E)-N-(2-(2-(2,6-dihydroxybenzylidene)hydrazinyl)-2-oxoethyl)-1-naphthamide;
(E)-N-(2-oxo-2-(2-(pyrimidin-4-ylmethylene)hydrazinyl)ethyl)-1-naphthamide;
(E)-N-(2-oxo-2-(2-(pyridin-2-ylmethylene)hydrazinyl)ethyl)-1-naphthamide;
(E)-N-(2-oxo-2-(2-(pyridin-4-ylmethylene)hydrazinyl)ethyl)-1-naphthamide;
(E)-N-(2-oxo-2-(2-(pyridin-3-ylmethylene)hydrazinyl)ethyl)-1-naphthamide;
(E)-N-(2-oxo-2-(2-(pyrimidin-2-ylmethylene)hydrazinyl)ethyl)-1-naphthamide;
(E)-N-(2-(2-((3-hydroxypyridin-2-yl)methylene)hydrazinyl)-2-oxoethyl)-1-naphthamide;
(E)-N-(2-(2-((3-hydroxypyridin-4-yl)methylene)hydrazinyl)-2-oxoethyl)-1-naphthamide;
(E)-N-(2-(2-((2-hydroxypyridin-3-yl)methylene)hydrazinyl)-2-oxoethyl)-1-naphthamide;
(E)-N-(2-(2-(2-aminobenzylidene)hydrazinyl)-2-oxoethyl)-1-naphthamide;
(E)-N-(2-(2-(3-aminobenzylidene)hydrazinyl)-2-oxoethyl)-1-naphthamide;
(E)-N-(2-(2-(4-aminobenzylidene)hydrazinyl)-2-oxoethyl)-1-naphthamide;
(E)-N-(2-(2-(2-fluorobenzylidene)hydrazinyl)-2-oxoethyl)-1-naphthamide;
(E)-N-(2-(2-(3-fluorobenzylidene)hydrazinyl)-2-oxoethyl)-1-naphthamide;
(E)-N-(2-(2-(4-fluorobenzylidene)hydrazinyl)-2-oxoethyl)-1-naphthamide;
(E)-N-(2-(2-(5-fluoro-2-hydroxybenzylidene)hydrazinyl)-2-oxoethyl)-1-naphthamide, and;
(E)-N-(2-(2-(2-hydroxy-5-methoxybenzylidene)hydrazinyl)-2-oxoethyl)-1-naphthamide and a pharmaceutically acceptable carrier.

Such pharmaceutical compositions may be used, for example, for interfering with the replication of herpesvirus as described herein.

In yet another aspect, the present invention relates to the use of a compound of formula IA or IB for interfering with herpesviruses replication or the use of such compound in the manufacture of a medicament for interfering with herpesviruses replication. In exemplary embodiments of the invention, the compound comprises formula IA or IB or may be selected, for example, from the group consisting of:

N-(2-(2-(2-hydroxy-5-methoxybenzylidene)hydrazino)-2-oxoethyl)-3-methyl-benzamide;
N-(2-(2-(2-hydroxybenzylidene)hydrazino)-2-oxoethyl)-1-naphthamide;
N-(2-(2-(3-allyl-2-hydroxybenzylidene)hydrazino)-2-v)-3-chlorobenzamide;
N-[2-(4-methoxyphenyl)ethyl]-2-[(1-phenyl-1H-tetrazol-5-yl)thio]acetamide;
1-(2-chloro-5-nitrophenyliminomethyl)-2-naphthol;
N-1H-tetrazol-5-yl-4-biphenylcarboxamide;
9-anthracenecarbaldehyde1H-tetrazol-5-ylhydrazone;
N-{[(2-methyl-2H-tetrazol-5-yl)amino]carbonothioyl}-2-thiophenecarboxamide;
N-(2-(2-(2-hydroxy-5-methoxybenzylidene)hydrazino)-2-oxoethyl)-1-naphthamide;
N-(2-(2-(3-allyl-2-hydroxybenzylidene)hydrazino)-2-oxoethyl)-2-chlorobenzamide;
N-(2-(2-(3-allyl-2-hydroxybenzylidene)hydrazino)-2-oxoethyl)-4-chlorobenzamide;
N-(2-(2-(3-allyl-2-hydroxybenzylidene)hydrazino)-2-oxoethyl)-1-naphthamide;
(E)-N-(2-(2-(2-hydroxybenzylidene)hydrazinyl)-2-oxoethyl)-1-naphthamide;
(E)-N-(2-(2-(3-hydroxybenzylidene)hydrazinyl)-2-oxoethyl)-1-naphthamide;
(E)-N-(2-(2-(4-hydroxybenzylidene)hydrazinyl)-2-oxoethyl)-1-naphthamide;
(E)-N-(2-(2-(3,4-dihydroxybenzylidene)hydrazinyl)-2-oxoethyl)-1-naphthamide;
(E)-N-(2-(2-(2,4-dihydroxybenzylidene)hydrazinyl)-2-oxoethyl)-1-naphthamide;
(E)-N-(2-(2-(2,6-dihydroxybenzylidene)hydrazinyl)-2-oxoethyl)-1-naphthamide;
(E)-N-(2-oxo-2-(2-(pyrimidin-4-ylmethylene)hydrazinyl)ethyl)-1-naphthamide;
(E)-N-(2-oxo-2-(2-(pyridin-2-ylmethylene)hydrazinyl)ethyl)-1-naphthamide;
(E)-N-(2-oxo-2-(2-(pyridin-4-ylmethylene)hydrazinyl)ethyl)-1-naphthamide;
(E)-N-(2-oxo-2-(2-(pyridin-3-ylmethylene)hydrazinyl)ethyl)-1-naphthamide;
(E)-N-(2-oxo-2-(2-(pyrimidin-2-ylmethylene)hydrazinyl)ethyl)-1-naphthamide;
(E)-N-(2-(2-((3-hydroxypyridin-2-yl)methylene)hydrazinyl)-2-oxoethyl)-1-naphthamide;
(E)-N-(2-(2-((3-hydroxypyridin-4-yl)methylene)hydrazinyl)-2-oxoethyl)-1-naphthamide;

(E)-N-(2-(2-((2-hydroxypyridin-3-yl)methylene)hydrazinyl)-2-oxoethyl)-1-naphthamide;
(E)-N-(2-(2-(2-aminobenzylidene)hydrazinyl)-2-oxoethyl)-1-naphthamide;
(E)-N-(2-(2-(3-aminobenzylidene)hydrazinyl)-2-oxoethyl)-1-naphthamide;
(E)-N-(2-(2-(4-aminobenzylidene)hydrazinyl)-2-oxoethyl)-1-naphthamide;
(E)-N-(2-(2-(2-fluorobenzylidene)hydrazinyl)-2-oxoethyl)-1-naphthamide;
(E)-N-(2-(2-(3-fluorobenzylidene)hydrazinyl)-2-oxoethyl)-1-naphthamide;
(E)-N-(2-(2-(4-fluorobenzylidene)hydrazinyl)-2-oxoethyl)-1-naphthamide;
(E)-N-(2-(2-(5-fluoro-2-hydroxybenzylidene)hydrazinyl)-2-oxoethyl)-1-naphthamide, and;
(E)-N-(2-(2-(2-hydroxy-5-methoxybenzylidene)hydrazinyl)-2-oxoethyl)-1-naphthamide.

In another aspect, the present invention relates to a method for interfering with herpesviruses replication from (in) a cell. The method may comprise contacting a cell infected by the herpesvirus with a compound of formula IA or IB or a compound selected from the group consisting of:

N-(2-(2-(2-hydroxy-5-methoxybenzylidene)hydrazino)-2-oxoethyl)-3-methyl-benzamide;
N-(2-(2-(2-hydroxybenzylidene)hydrazino)-2-oxoethyl)-1-naphthamide;
N-(2-(2-(3-allyl-2-hydroxybenzylidene)hydrazino)-2-v)-3-chlorobenzamide;
N-[2-(4-methoxyphenyl)ethyl]-2-[(1-phenyl-1H-tetrazol-5-yl)thio]acetamide;
1-(2-chloro-5-nitrophenyliminomethyl)-2-naphthol;
N-1H-tetrazol-5-yl-4-biphenylcarboxamide;
9-anthracenecarbaldehyde1H-tetrazol-5-ylhydrazone;
N-{[(2-methyl-2H-tetrazol-5-yl)amino]carbonothioyl}-2-thiophenecarboxamide;
N-(2-(2-(2-hydroxy-5-methoxybenzylidene)hydrazino)-2-oxoethyl)-1-naphthamide;
N-(2-(2-(3-allyl-2-hydroxybenzylidene)hydrazino)-2-oxoethyl)-2-chlorobenzamide;
N-(2-(2-(3-allyl-2-hydroxybenzylidene)hydrazino)-2-oxoethyl)-4-chlorobenzamide;
N-(2-(2-(3-allyl-2-hydroxybenzylidene)hydrazino)-2-oxoethyl)-1-naphthamide;
(E)-N-(2-(2-(2-hydroxybenzylidene)hydrazinyl)-2-oxoethyl)-1-naphthamide;
(E)-N-(2-(2-(3-hydroxybenzylidene)hydrazinyl)-2-oxoethyl)-1-naphthamide;
(E)-N-(2-(2-(4-hydroxybenzylidene)hydrazinyl)-2-oxoethyl)-1-naphthamide;
(E)-N-(2-(2-(3,4-dihydroxybenzylidene)hydrazinyl)-2-oxoethyl)-1-naphthamide;
(E)-N-(2-(2-(2,4-dihydroxybenzylidene)hydrazinyl)-2-oxoethyl)-1-naphthamide;
(E)-N-(2-(2-(2,6-dihydroxybenzylidene)hydrazinyl)-2-oxoethyl)-1-naphthamide;
(E)-N-(2-oxo-2-(2-(pyrimidin-4-ylmethylene)hydrazinyl)ethyl)-1-naphthamide;
(E)-N-(2-oxo-2-(2-(pyridin-2-ylmethylene)hydrazinyl)ethyl)-1-naphthamide;
(E)-N-(2-oxo-2-(2-(pyridin-4-ylmethylene)hydrazinyl)ethyl)-1-naphthamide;
(E)-N-(2-oxo-2-(2-(pyridin-3-ylmethylene)hydrazinyl)ethyl)-1-naphthamide;
(E)-N-(2-oxo-2-(2-(pyrimidin-2-ylmethylene)hydrazinyl)ethyl)-1-naphthamide;
(E)-N-(2-(2-((3-hydroxypyridin-2-yl)methylene)hydrazinyl)-2-oxoethyl)-1-naphthamide;
(E)-N-(2-(2-((3-hydroxypyridin-4-yl)methylene)hydrazinyl)-2-oxoethyl)-1-naphthamide;
(E)-N-(2-(2-((2-hydroxypyridin-3-yl)methylene)hydrazinyl)-2-oxoethyl)-1-naphthamide;
(E)-N-(2-(2-(2-aminobenzylidene)hydrazinyl)-2-oxoethyl)-1-naphthamide;
(E)-N-(2-(2-(3-aminobenzylidene)hydrazinyl)-2-oxoethyl)-1-naphthamide;
(E)-N-(2-(2-(4-aminobenzylidene)hydrazinyl)-2-oxoethyl)-1-naphthamide;
(E)-N-(2-(2-(2-fluorobenzylidene)hydrazinyl)-2-oxoethyl)-1-naphthamide;
(E)-N-(2-(2-(3-fluorobenzylidene)hydrazinyl)-2-oxoethyl)-1-naphthamide;
(E)-N-(2-(2-(4-fluorobenzylidene)hydrazinyl)-2-oxoethyl)-1-naphthamide;
(E)-N-(2-(2-(5-fluoro-2-hydroxybenzylidene)hydrazinyl)-2-oxoethyl)-1-naphthamide, and;
(E)-N-(2-(2-(2-hydroxy-5-methoxybenzylidene)hydrazinyl)-2-oxoethyl)-1-naphthamide.

In yet another aspect, the present invention provides a method of treating herpesvirus infection. The method may comprise administering a compound or a pharmaceutically acceptable salt thereof to a mammal in need. The compound or salt may comprise formula IA or IB or may be selected from the group consisting of:

N-(2-(2-(2-hydroxy-5-methoxybenzylidene)hydrazino)-2-oxoethyl)-3-methyl-benzamide;
N-(2-(2-(2-hydroxybenzylidene)hydrazino)-2-oxoethyl)-1-naphthamide;
N-(2-(2-(3-allyl-2-hydroxybenzylidene)hydrazino)-2-v)-3-chlorobenzamide;
N-[2-(4-methoxyphenyl)ethyl]-2-[(1-phenyl-1H-tetrazol-5-yl)thio]acetamide;
1-(2-chloro-5-nitrophenyliminomethyl)-2-naphthol;
N-1H-tetrazol-5-yl-4-biphenylcarboxamide;
9-anthracenecarbaldehyde1H-tetrazol-5-ylhydrazone;
N-{[(2-methyl-2H-tetrazol-5-yl)amino]carbonothioyl}-2-thiophenecarboxamide;
N-(2-(2-(2-hydroxy-5-methoxybenzylidene)hydrazino)-2-oxoethyl)-1-naphthamide;
N-(2-(2-(3-allyl-2-hydroxybenzylidene)hydrazino)-2-oxoethyl)-2-chlorobenzamide;
N-(2-(2-(3-allyl-2-hydroxybenzylidene)hydrazino)-2-oxoethyl)-4-chlorobenzamide;
N-(2-(2-(3-allyl-2-hydroxybenzylidene)hydrazino)-2-oxoethyl)-1-naphthamide;
(E)-N-(2-(2-(2-hydroxybenzylidene)hydrazinyl)-2-oxoethyl)-1-naphthamide;
(E)-N-(2-(2-(3-hydroxybenzylidene)hydrazinyl)-2-oxoethyl)-1-naphthamide;
(E)-N-(2-(2-(4-hydroxybenzylidene)hydrazinyl)-2-oxoethyl)-1-naphthamide;
(E)-N-(2-(2-(3,4-dihydroxybenzylidene)hydrazinyl)-2-oxoethyl)-1-naphthamide;
(E)-N-(2-(2-(2,4-dihydroxybenzylidene)hydrazinyl)-2-oxoethyl)-1-naphthamide;
(E)-N-(2-(2-(2,6-dihydroxybenzylidene)hydrazinyl)-2-oxoethyl)-1-naphthamide;
(E)-N-(2-oxo-2-(2-(pyrimidin-4-ylmethylene)hydrazinyl)ethyl)-1-naphthamide;
(E)-N-(2-oxo-2-(2-(pyridin-2-ylmethylene)hydrazinyl)ethyl)-1-naphthamide;
(E)-N-(2-oxo-2-(2-(pyridin-4-ylmethylene)hydrazinyl)ethyl)-1-naphthamide;

(E)-N-(2-oxo-2-(2-(pyridin-3-ylmethylene)hydrazinyl)ethyl)-1-naphthamide;

(E)-N-(2-oxo-2-(2-(pyrimidin-2-ylmethylene)hydrazinyl)ethyl)-1-naphthamide;

(E)-N-(2-(2-((3-hydroxypyridin-2-yl)methylene)hydrazinyl)-2-oxoethyl)-1-naphthamide;

(E)-N-(2-(2-((3-hydroxypyridin-4-yl)methylene)hydrazinyl)-2-oxoethyl)-1-naphthamide;

(E)-N-(2-(2-((2-hydroxypyridin-3-yl)methylene)hydrazinyl)-2-oxoethyl)-1-naphthamide;

(E)-N-(2-(2-(2-aminobenzylidene)hydrazinyl)-2-oxoethyl)-1-naphthamide;

(E)-N-(2-(2-(3-aminobenzylidene)hydrazinyl)-2-oxoethyl)-1-naphthamide;

(E)-N-(2-(2-(4-aminobenzylidene)hydrazinyl)-2-oxoethyl)-1-naphthamide;

(E)-N-(2-(2-(2-fluorobenzylidene)hydrazinyl)-2-oxoethyl)-1-naphthamide;

(E)-N-(2-(2-(3-fluorobenzylidene)hydrazinyl)-2-oxoethyl)-1-naphthamide;

(E)-N-(2-(2-(4-fluorobenzylidene)hydrazinyl)-2-oxoethyl)-1-naphthamide;

(E)-N-(2-(2-(5-fluoro-2-hydroxybenzylidene)hydrazinyl)-2-oxoethyl)-1-naphthamide, and;

(E)-N-(2-(2-(2-hydroxy-5-methoxybenzylidene)hydrazinyl)-2-oxoethyl)-1-naphthamide.

Further aspects of the invention relates to compounds that may be useful in the manufacture of the compounds of formula IA described herein. Such compounds may have, for example, formula IA¹ or IA²:

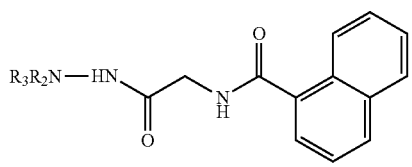

IA¹

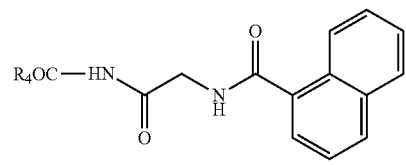

IA² where R₂ and R₃ may independently be H or an alkyl group of 1 to 6 carbon atoms and;

where R₄ may be, for example H or an alkyl group of 1 to 6 carbon atoms.

Yet further aspects of the invention encompass the use of the compounds of formula IA¹ and IA² in the manufacture of a herpesvirus DNA polymerase ligand or in the manufacture of a herpesvirus inhibitor, especially inhibitors of herpes simplex 1, herpes simplex 2, varicella zoster virus or cytomegalovirus. Compounds of formulas IA¹ or IA² may be used for the manufacture of a compound of formula IA.

Further aspects of the invention relates to compounds that may be useful in the manufacture of the compounds of formula IB. Such compounds may have, for example, formula IB¹ or IB²:

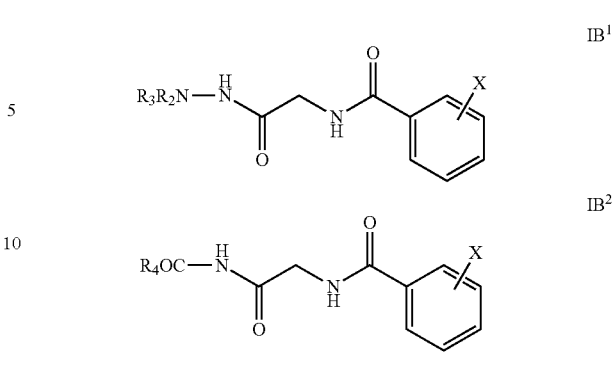

where $R_2$ and $R_3$ may independently be H or an alkyl group of 1 to 6 carbon atoms;

wherein $R_4$ may be, for example H or an alkyl group of 1 to 6 carbon atoms;

where X may be selected, for example, from the group consisting of H, —$OR_1$, $NH_2$, F, Cl, Br, I, an alkyl group of 1 to 3 carbon atoms and an allyl group and;

where $R_1$ may be selected from the group consisting of H or an alkyl group of 1 to 3 carbon atoms.

Yet further aspects of the invention encompass the use of the compounds of formula IB¹ and IB² in the manufacture of a herpesvirus DNA polymerase ligand or in the manufacture of a herpesvirus inhibitor, especially inhibitors of herpes simplex 1, herpes simplex 2, varicella zoster virus or cytomegalovirus. Compounds of formulas IB¹ or IB² may be used for the manufacture of a compound of formula IB.

In an additional aspect, the present invention relates to the use of a compound of formula IA or IB in the manufacture of a herpesvirus DNA polymerase ligand or a herpesvirus inhibitor.

As used herein, the term "lower alkyl" can be straight-chain or branched having from 1 to 6 carbon atoms.

It is to be understood herein that a "straight alkyl group of 1 to 6 carbon atoms" includes for example, methyl, ethyl, propyl, butyl, pentyl, hexyl.

It is to be understood herein that a "branched alkyl group of 3 to 6 carbon atoms" includes for example, without limitation, iso-butyl, tert-butyl, 2-pentyl, 3-pentyl, etc.

It is to be understood herein, that a "cycloalkyl group having 3 to 6 carbon" includes for example, without limitation, cyclopropyl, cyclobutyl, cyclopentyl, cyclohexyl (i.e., $C_6H_{11}$).

Salts derived from appropriate bases include alkali metal (e.g., sodium), alkaline earth metal (e.g., magnesium), ammonium and N—$(C_{1-4}\ alkyl)_4^+$ salts.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

Examples of base addition salts include but are not limited to alkali metal salts and alkaline earth metal salts. Non-limiting examples of alkali metal salts include lithium, sodium and potassium salts. Non-limiting examples of alkaline earth metal salts include magnesium and calcium salts.

This invention also envisions the quaternization of any basic nitrogen containing groups of the compounds disclosed herein. The basic nitrogen may be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

Pharmaceutically acceptable carrier includes for example and without limitation alumina, aluminum stearate, lecithin, serum proteins, such as human serum albumin, buffer substances such as phosphates, glycine, sorbic acid, potassium sorbate, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyoxyethylene-polyoxypropylene-block copolymers, and polyethylene glycol.

EXAMPLE 1

Materials and Methods

To discover new viral DNA polymerase inhibitors, we used a rational approach called structure-based inhibitor design.

Docking Site Selection and Pre-Docking Preparation:

The recently-determined 3D model of CMV DNA pol determined by our group [8] and the recent crystal structure of HSV-1 DNA polymerase (pdb id 2GV9) [9] served as receptors for docking. Hydrophobic pockets on the crystal structure of the HSV-1 DNA polymerase in non replicating state (pdb 2GV9) [9] were calculated with the Site Finder application under Molecular Application Environment (MOE) program (Chemical Computing Group, Montreal, Canada), and ranked according to their hydrophobic contacts and their location. Two magnesium atoms that were missing in the crystal structure coordinates of HSV1 DNA polymerase (2GV9) were modeled in the catalytic site. Water molecules were removed and hydrogen atoms were added, and the protein was inspected visually for accuracy in the $\chi^2$ dihedral angle of Asn and H is residues and the $\chi^3$ angle of Gln, and rotated by 180 degree when needed to maximize hydrogen bonding. The proper H is tautomer was also manually selected to maximize hydrogen bonding. All Asp, Glu, Arg and Lys were usually left in their charged state.

Ligand docking in the DNA pol selected docking site was carried out with the GOLD version 3.2 [10]. Ligand and side-chain flexibility was allowed during docking. The ChemScore function estimates the free energy of ligand binding to a protein as follows: ChemScore=$\Delta G_{binding}$+$P_{clash}$+$c_{internal}P_{internal}$+($P_{covalent}C_{covalent}$+$P_{constrain}$) with $\Delta G_{binding}$=$\Delta G_0$+$\Delta G_{hbond}S_{hbond}$+$\Delta G_{metal}S_{metal}$+$\Delta G_{lipo}S_{lipo}$+$\Delta G_{rot}H_{rot}$, where $S_{hbond}$, $S_{metal}$, and $S_{lipo}$ are scores for hydrogen bonding, acceptor-metal, and lipophilic interactions, respectively. $H_{rot}$ represents the loss of conformational entropy of the ligand upon binding to the protein [11].

Virtual Screening:

A free public database "ZINC 6" [12] was selected for virtual screening. A subset of 128 000 compounds with drug-like properties satisfying the Lipinski rules of 5 [13] was selected. The database was used for virtual screening into the selected docking site and the compounds were scored according to ChemScore function [11]. In the docking simulation with HSV-1 DNA pol, compounds were ranked according to the ChemScore and hydrogen bonding potential.

Antiviral Compounds:

Top leading compounds were purchased from Sigma-Aldrich or ChemBridge for in vitro testing. On the day of the assay, compounds were prepared in DMSO at a concentration of 10 mM. Stock solutions were then diluted in Eagle's minimal essential medium (MEM) to the appropriate concentrations. ACV, GCV and FOS (prepared in MEM) were used as comparators for susceptible and resistant recombinant viruses and clinical isolates.

Cells and Viruses:

Human foreskin fibroblasts (HFFs) and African green monkey kidney cells (Vero) were grown in MEM supplemented with 10% fetal bovine serum. Cells were maintained at 37° C. in a humidified 5% $CO_2$ atmosphere. Vero cells and HFFs were used for propagation of viral strains and susceptibility assays for HSV-1/HSV-2 and VZV/CMV, respectively. Clinical strains H25 (HSV-1), HSV22 (HSV-2) as well as laboratory strains KOS(HSV-1), Ellen (VZV) and AD169 (CMV) were used as wild-type susceptible reference isolates. Clinical strains C119629 (HSV-1), C114093 (HSV-1), C80249 (HSV-1), L920062 (HSV-1), MS2 (HSV-2), C75134 (HSV-2), W-940012 (HSV-2), C72984 (HSV-2), D-900180 (HSV-2), M-890546 (HSV-2), P-920056 (HSV-2) and GB2000VZV (VZV) as well as laboratory strains Xbaf (CMV) and VQA3 (CMV) were used as drug (ACV/GCV/FOS)— resistant isolates [14-16]. All clinical strains starting with the letter C originated from the Quebec City clinical virology laboratory.

Cytotoxicity Assays:

Toxicity of compounds 1 to 8 as well as derivatives of compounds 2 and 3 was assessed on Vero cells and HFFs using the CellTiter 96 Aqueous Non-Radioactive Cell Proliferation Assay protocol (Promega, Madison, Wis.). This assay is based on the use of solutions of a tetrazolium salt (3-(4,5-dimethylthiazol-2-yl)-5-(3-carboxymethoxyphenyl)-2-(4-sulphophenyl)-2H-tetrazolium, inner salt; MTS) and an electron coupling reagent (phenazine methosulfate; PMS). The tetrazolium salt is reduced by living cells to yield a formazan product that can be assayed colorimetrically. Briefly, HFFs and Vero cells were seeded in 96-well plates. After 24 h, media was aspirated and 100 µl of compounds diluted in MEM at concentrations up to 100 µM were added to wells in quaduplicate. After incubation at 37° C. for 3 days, 10 µl of a solution of MTS and PMS were added to each well. The plates were incubated at 37° C. for 2 h. The absorbance of the supernatant was read at a wavelength of 492 nm to measure cell viability compared to no-drug control wells. The drug concentration was plotted against the optical density of each sample and cellular toxicity ($CC_{50}$) was calculated using GraphPad Prism version 5.0 (GraphPad Inc., La Jolla, Calif., USA).

Antiviral Assays:

Antiviral activity of compounds 1 to 8 was first tested at two concentrations, i.e. 1 µM and 10 µM, along with currently-available first-line drugs (ACV for HSV/VZV and GCV for CMV). Then, 50% inhibitory concentration ($IC_{50}$) values were determined for the top leading compounds in comparison with ACV, GCV and FOS using a standard plaque reduction assay (PRA) [17]. Briefly, Vero cells or HFFs seeded in 24-well plates were inoculated with 40 plaque forming units (PFUs) of recombinant viruses or clinical isolates. Infected cells were incubated with serial drug concentrations for appropriate periods of time. Cells were fixed and stained. The number of plaques was counted in each well and expressed in percentage of the PFUs in no-drug control wells. Recombinant and clinical viral strains were considered resistant to a drug if their $IC_{50}$ values were at least 2.5 times greater than that of the representative wild-type strains.

Microsomal Stability:

Sprague-Dawley rat liver microsomes (concentration 1 mg/ml) were incubated at 37° C. with 2 µM of compounds 2 or 3 in PBS containing 5 mM $MgCl_2$ and 1 mM NADPH. The antihypertensive drug reserpine was used as a reference compound. Aliquots of 50 µl were withdrawn at different time intervals and placed in 96-well plates containing 50 µL of acetonitrile on ice. Samples were then mixed and centrifuged at 3000 rpm and 10 µL were injected in a liquid chromatography system (Agilent 1100 Binary Pumps). The aliquots from liquid chromatography were subjected to mass spectrometry analysis on SCIEX API4000 with TurboIonSpray ionization source to determine the remaining percentage of the parent compound. Intrinsic clearance ($Cl_{int}$) estimates were determined using the rate of parent compound disappearance. The slope (-k) was determined by linear regression analysis from the linear portion of the natural logarithm of the test compound concentration versus time plot. The elimination rate constant ($t_{1/2}$) was calculated according to k=ln $2/t_{1/2}$. The microsomal $Cl_{int}$ can be derived from the equation $Cl_{int}$=kVfu (mL/min/mg protein) where fu is the unbound fraction and V is the volume of the incubation expressed in milliliters per mg of microsomal protein. As fu is not known for the tested compounds, the calculation was performed with fu=1 (V). The $Cl_{int}$ was also extrapolated to the whole liver protein.

Membrane Permeability Measurement:

Passive membrane permeability was determined using Parallel Artificial Membrane Permeability Assay (PAMPA) [18]. Initial concentrations of compounds 2 and 3 used for this assay were 37 and 2.5 respectively. Membrane area was 0.3 $cm^2$. After a 5 h incubation, fractions were taken on both sides of the membrane and compound concentrations were determined by LC-MS/MS. The apparent permeability coefficient ($P_{app}$) was calculated using the equation $P_{app}=(dQ/dtAc_0)$, where dQ/dt is the appearance rate of compound in the acceptor compartment, A is the surface area of the transwell membrane, and $c_o$ is the initial concentration in the donor compartment.

EXAMPLE 2

Virtual Screening and Molecular Modeling

Figure 3:
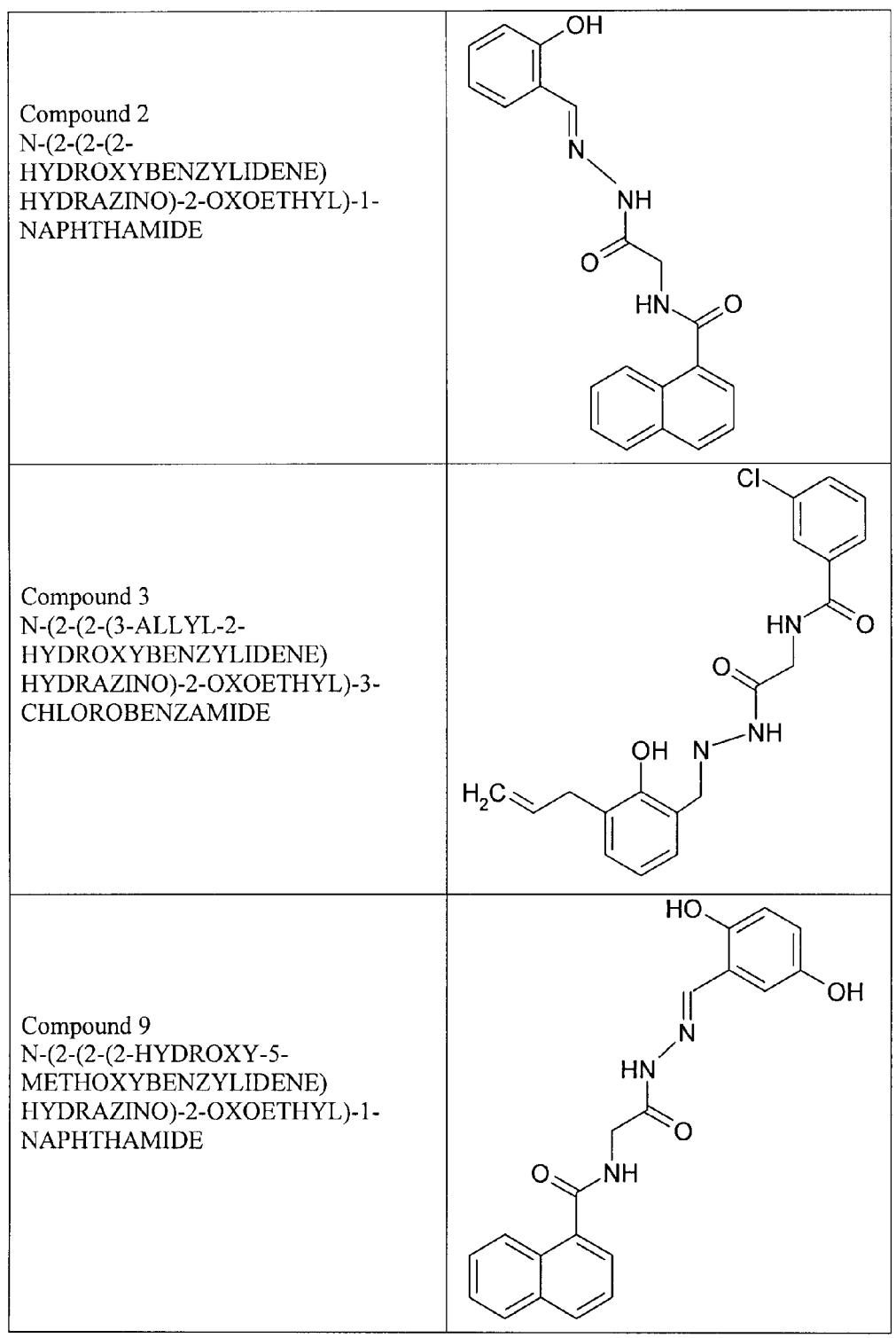
FIG. 3 is a table showing the chemical structure of compounds having a high affinity with the viral DNA polymerase active site near $Mg^{2+}$.
Figure 4A:
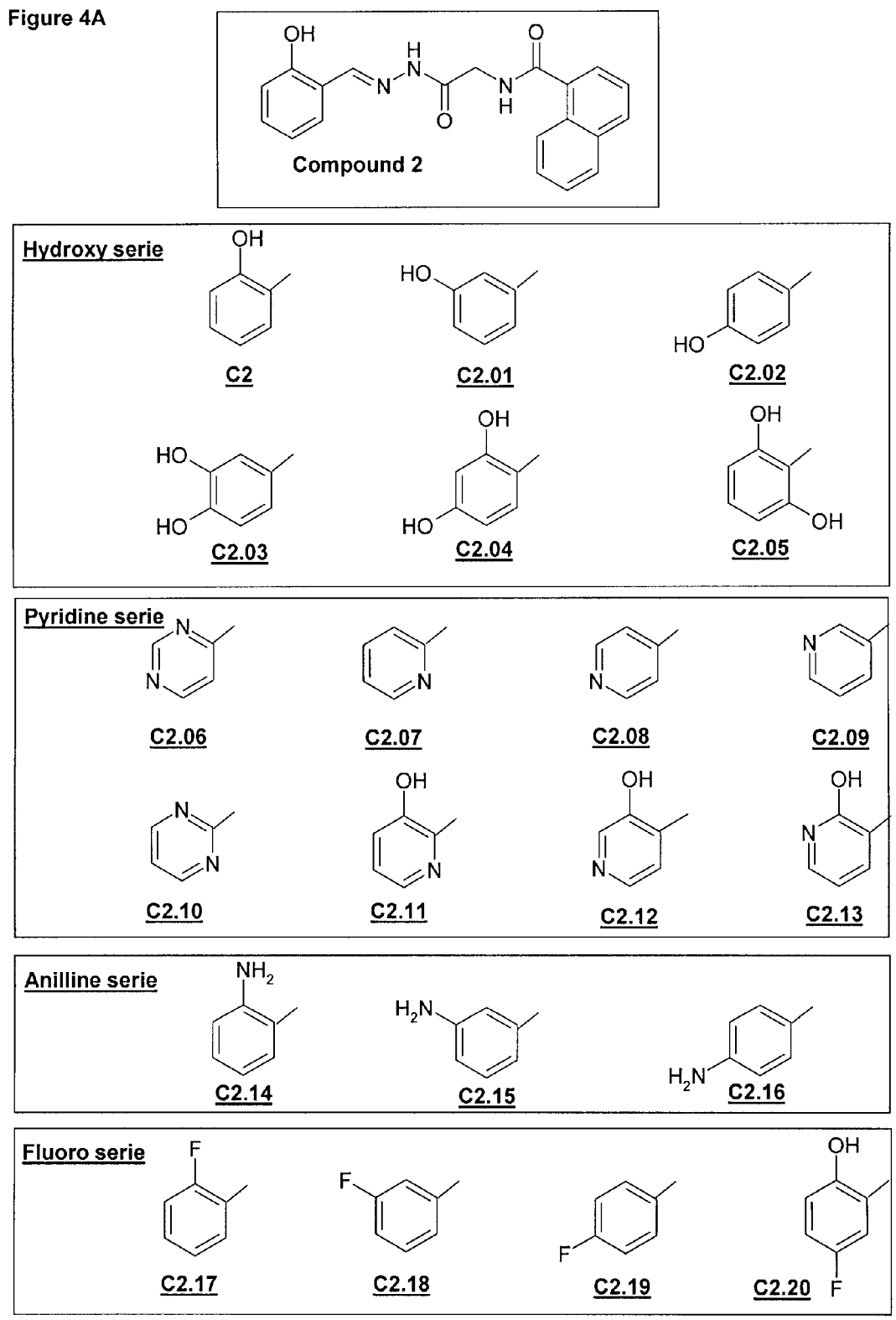
FIG. 4A represents the structure of compound 2 derivatives.

To discover new viral DNA pol inhibitors, we used a rational approach called structure-based inhibitor design. The recently-determined 3D model of CMV DNA pol determined by our group and the recent crystal structure of HSV-1 DNA pol (pdb id 2GV9) served as receptors for docking. Two $Mg^{2+}$ atoms were modeled in the active site of the HSV-1 crystal structure to complete the catalytic site. A docking site, was selected from a number of potential sites suggested by the Site Finder utility of the program MOE. Other potential sites were not considered because they were too far (>15 Å) from the DNA binding site. The selected site is located in the vicinity of the active site in a pocket close to the $Mg^{2+}$ atoms and delimited by residues Val715, Asp717, Ser720, Arg785, Lys811, Asn815, Tyr884, Lys939 (FIG. 1). Virtual screening of a large database of commercially-available compounds was performed inside a sphere delimited by 10 Å radius around Val715 CB atom, which is located near the center of the selected pocket. The top 50 ranking compounds were selected and their location in the active site was inspected. Further selection left only 12 compounds that have a predicted binding location close to the $Mg^{2+}$ atoms. Selected compounds were purchased and tested for antiviral activity (see FIG. 2 for list of compounds and FIG. 3 for chemical structure of lead compounds). Twenty new chemical entity derivatives of lead compound 2 with substitution on the hydroxyl benzyldiene group were also designed (FIGS. 4A and 4B) and docked to evaluate their binding energy. Many compound derivatives have better predicted binding energy than lead compound 2 (FIG. 4C). New derivatives of compound 2 (i.e. compounds C2.05, C2.11 and C2.20) and two derivatives of compound 3 (i.e. compounds C3-1 and C3-2) (FIG. 5), which are all new chemical entities, were selected for chemical synthesis.

Toxicity of Compounds:

Toxicity of compounds 1 to 8 was evaluated on HFFs and Vero cells using a MTS assay. Compounds 1 to 8 were not toxic on both cell lines at the highest concentration tested (i.e. 100 µM) after an incubation period of 3 days (see FIG. 6 for cell toxicity of lead compounds 2 and 3).

Activity of Compounds:

Antiviral activity of compounds 1 to 8 was first tested at two concentrations (1 µM and 10 µM) along with currently-available first-line drugs (ACV for HSV/VZV and GCV for CMV) using a standard PRA. The relative activity (% viral plaques relative to control with no antiviral) for compounds 1 to 8 against HSV-1, HSV-2, VZV and CMV representative strains is presented in FIGS. 7A and 7B.

$IC_{50}$ values were determined for compounds 2, 3 and 9 (most active drugs) along with commercial compounds against a panel of wild-type HSV-1, HSV-2, VZV and CMV strains (FIG. 8). Compound 2 was slightly less active than ACV (by a factor of 2 to 3-fold) against representative strains of HSV and VZV while compound 3 was also slightly less active than GCV (by a factor of 2-fold) against CMV reference strain. Compound 9 was also less active than ACV (by a factor of 3 to 4-fold) against representative strains of HSV.

Antiviral Activity of Compound 2 Against Drug-Resistant HSV-1 and HSV-2 Strains:

A more detailed evaluation of the activity of compound 2 against a series of wild-type as well as ACV- and/or FOS-resistant HSV clinical isolates and recombinant strains was performed in Vero cells using a standard PRA (see FIGS. 9 and 10 for HSV-1 and HSV-2, respectively). Compound 2 retained full antiviral activity against ACV- and/or FOS-resistant HSV-1 and HSV-2 strains with $IC_{50}$ value increases of 0.7 to 1.7-fold compared to the representative wild-type strains.

Antiviral Activity of Compound 2 Against Wild-Type and Drug-Resistant VZV Strains:

Antiviral activity of compound 2 against a wild-type VZV strain and an ACV-resistant clinical isolate was evaluated in HFF cells using a standard PRA (FIG. 11). This compound retained full antiviral activity against ACV-resistant VZV strain with an IC$_{50}$ value increase of 0.6 compared to the reference drug-susceptible strain.

Antiviral Activity of Compound 3 Against Drug-Resistant CMV Strains:

Evaluation of antiviral activity of compound 3 against wild-type as well as GCV- and/or FOS-resistant CMV clinical isolates and recombinant strains was also performed in HFF cells using a standard PRA (FIG. 12). Compound 3 retained activity against GCV- and/or FOS-resistant CMV strains with IC$_{50}$ value increases of 1 to 2-fold compared to the representative wild-type strain.

Membrane Permeability:

PAMPA assesses passive diffusion of a molecule, the most common pathway for drug absorption and uptake by target tissues. In this assay, permeability of compounds can be classified as low ($P_{app}(\times 10^{-6}$ CM/S)<1), intermediate (1<$P_{app}$<10), or high ($P_{app}$>10). PAMPA was used to predict membrane permeability for lead compounds 2 and 3. Compound 2 shows high permeability with $P_{app}$=11.3±1.17×10$^{-6}$ cm/s (n=4) while compound 3 has intermediate permeability with $P_{app}$=3.4±0.45×10$^{-6}$ cm/s (n=4) (FIG. 13).

Microsomal Stability:

Metabolic stability of compounds 2 and 3 was evaluated using rat liver microsomes. Samples were taken at defined time points and the percentage of unmetabolized parent compound was determined by LC-MS/MS. Half-life and intrinsic clearance were evaluated and compared to the reference compound reserpine (FIG. 14). Half-life ($t_{1/2}$) values of 33 and 22 min as well as intrinsic clearance (Cl$_{int}$) extrapolated to whole rat liver of 37 and 62 ml/min/kg proteins were obtained for compounds 2 and 3, respectively. In comparison, $t_{1/2}$ and Cl$_{int}$ were 43 min and 28 ml/min/kg for reserpine.

Antiviral Activity of Compounds 2 and 3 Derivatives Against Herpesviruses Strains:

Three derivatives of compound 2 (i.e., compounds C2.05, C2.11 and C2.20) and two derivatives of compound 3 (C3-1 and C3-2), which are new chemical entities selected for synthesis, were evaluated against HSV-1, HSV-2, VZV and CMV strains by PRA (FIG. 15). Derivative C2.20 was as active against wild-type HSV-1 and HSV-2 as well as ACV-resistant VZV strains as compound 2. Derivative C2.11 was also active against wild-type HSV-2 and ACV-resistant VZV strains, but not against HSV-1. Derivative C2.05 was active against wild-type HSV-2 only. Compound 2 derivatives C2.05, C2.11 and C2.20 were not active against the wild-type CMV isolate. Compound 3 derivatives C3-1 and C3-2 were not active against any herpesvirus strains at the concentrations tested.

Cellular Toxicity of Compounds 2 and 3 and their Derivatives:

Toxicity of compound 2, compound 3 and their derivatives along with ACV, GCV and FOS was assessed on Vero cells and HFFs using a MTS cell proliferation assay and the concentration which inhibited 50% of cell viability (CC$_{50}$) was calculated (FIG. 16). In both cell lines, compound 2, compound 3 and their derivatives were somewhat more toxic than ACV, GCV and FOS. Nevertheless, the therapeutic index values (CC$_{50}$/IC$_{50}$) of compound 2 and C2.20 were 19.3 and 9.6, respectively, for Vero cells using the IC$_{50}$ values of the HSV-1 reference strain (H25) whereas the therapeutic index of compound 3 was 6.6 for HFFs using the IC$_{50}$ value of the CMV reference strain (AD169).

Infections by herpesviruses such as HSV, VZV and CMV are associated with significant morbidity in immunocompetent subjects and even mortality in severely immunocompromised hosts. Except for VZV, there are currently no vaccines commercially-available for preventing herpesvirus infections. Furthermore, because of the establishment of viral latency in immune-preserved sites, infected individuals are subjected to lifelong recurrent infections. Antiviral agents remain the best strategy to treat and also prevent clinical viral reactivations. However, as for all antivirals, drug resistance is now a significant problem in immunocompromised patients exposed to prolonged antiviral therapy. Thus, there is an urgent and unmet need for developing anti-herpesvirus agents with different mechanisms of action.

In the present study, virtual screening of a drug-like compound library was done against a newly-described HSV-1 DNA polymerase pocket near the active site. Twelve non-nucleoside compounds were selected from screening and tested in vitro. Compound 2 was identified as a highly active inhibitor against HSV-1, -2 and VZV and to a lesser extent against CMV. Compound 3 was also highly active against CMV. The in vitro activity of these two compounds was almost comparable (2 to 3-fold higher IC$_{50}$ values) than conventional drugs, such as ACV and GCV against wild-type isolates. Remarkably, these two compounds were also active against drug-resistant strains isolated from patients or generated in vitro. Of note, both compounds displayed good cell permeability, low cell toxicity and good metabolic stability. New chemical entity derivatives of compounds 2 and 3 with binding potential to the HSV-1 DNA polymerase pocket (based on ChemScore) were synthetized and tested for antiviral activity in cell cultures. Compound C2.20 retained excellent activity against HSV-1, HSV-2 and VZV like the parental compound, including against strains resistant to current antiviral agents. Compound 2 derivatives listed in FIG. 4C having a Chemscore rank closed to that of compound 2 are likely to have a similar or better activity than the parent compound. This suggests that the new compounds bind to the viral DNA pol at a different site than nucleoside or pyrophosphate analogues probably through interactions with residues Tyr884, Val715, Lys939, Tyr722 and the two Mg$^{2+}$ atoms.

EXAMPLE 3

Chemical Synthesis

Figure 17:
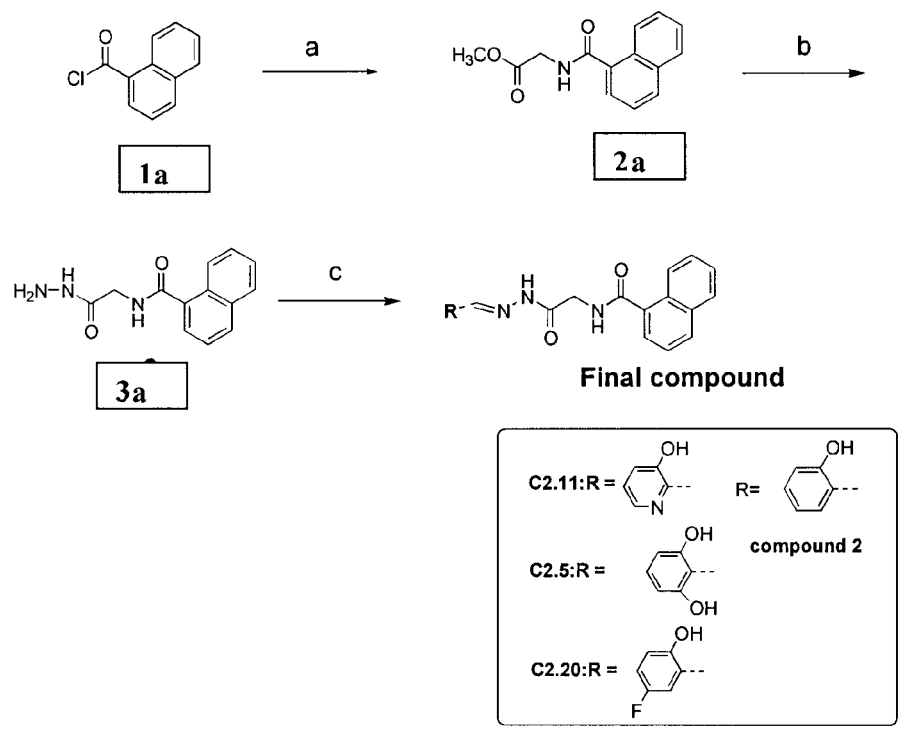
FIG. 17 is a scheme representing the chemical synthesis of compound 2 and derivative compounds C2.05, C2.11, and C2.20.
Figure 18:
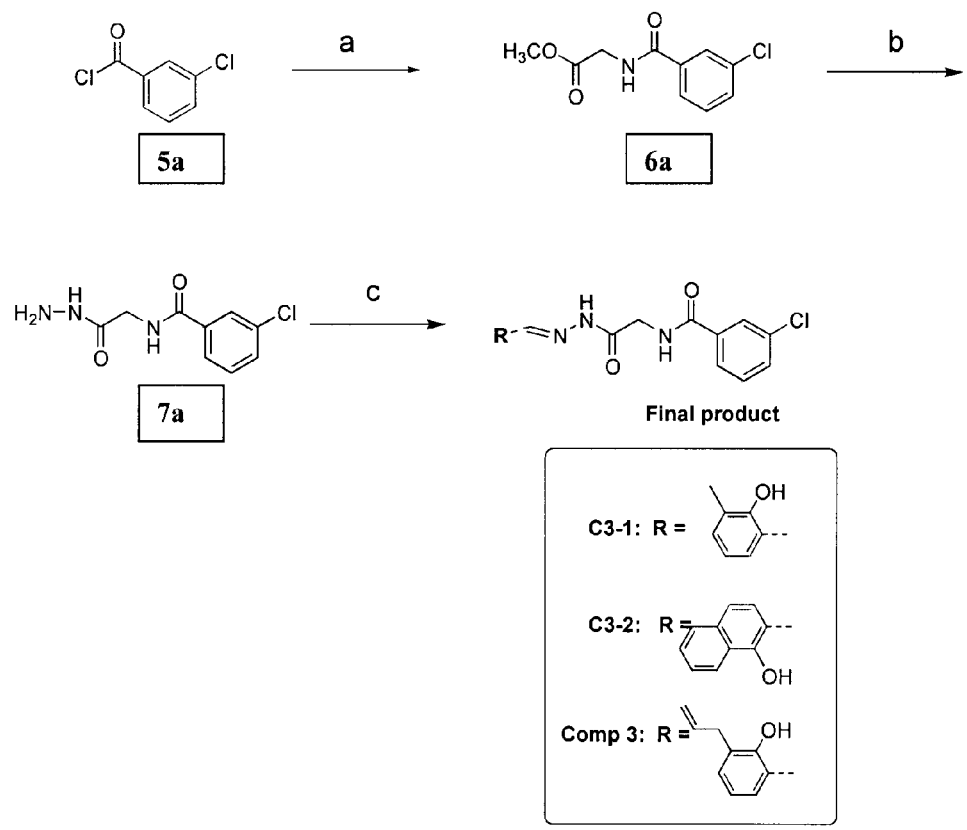
FIG. 18 is a scheme representing the chemical synthesis of compound 3 and derivative compounds C3-1 and C3-2.

The method of preparation of compounds 2 and 3 and selected derivatives is illustrated in FIGS. 17 and 18 respectively.

Procedures for the Preparation of Naphthalene-Hydrazide Derivatives (Scheme Synthesis of Compound 2 and Derivatives)

Step a: Preparation of methyl-N-(naphthalen-1-ylcarbonyl)glycinate (2a)

To a suspension of methylglycinate hydrochloride (3.3 g, 26 mmol) in THF (100 mL) was added at 0° C. triethylamine (11 mL, 78 mmol). After stirring for 5 min, 1-naphthaloyl-chloride (4.5 mL, 31.5 mmol) was added dropwise and the resulting mixture was stirred overnight at room temperature. 10% HCl was added and the aqueous phase extracted with EtOAc. The combined organic phases were washed with 10% NaOH, brine and concentrated under vacuum. The crude compound was purified by flash chromatography using DCM/EtOAc (98:2) as eluent to give the compound 2a (5 g, 79%). $^1$H NMR (acetone-d$_6$) δ 3.76 (s, 3H, OMe), 4.24 (d, J=6.0 Hz, 2H, CH$_2$), 7.52-7.58 (m, 3H, Ar), 7.72 (dd, J=1.1 and 7.0 Hz, 1H, Ar), 7.90 (m, 1H, Ar), 8.01 (d, J=8.3 Hz, 2H, Ar), 8.46 (m, 1H, NH); $^{13}$C NMR (acetone-d$_6$) δ 41.91 (CH$_2$), 52.22 (OMe), 125.67, 126.07, 126.66, 127.09, 127.49, 128.99, 131.09, 131.22, 134.57, 135.36, 170.12 (CO), 171.13 (CO).

Step b: Preparation of N-(2-hydrazinyl-2-oxoethyl) napthalene-1-carboxamide (3a)

The above compound 2a (3.3 g, 13.1 mmol) was heated at 60° C. with hydrazine hydrate (3.5 mL, 65 mmol) in EtOH (30 mL) for 2 hours. After cooling at room temperature, water (10 mL) was added. The resulting white precipitate was filtered and dried under vacuum to give hydrazide derivative 3a (2.6 g, 79%). $^1$H NMR (acetone-d$_6$) δ 3.91 (d, J=5.9 Hz, 2H, CH$_2$), 7.55-7.58 (m, 3H, Ar), 7.68 (dd, J=1.1 and 7.0 Hz, 1H, Ar), 7.98 (d, J=8.0 Hz, 1H, Ar), 8.02 (d, J=8.3 Hz, 2H, Ar), 8.35 (m, 1H, NH), 8.74 (t, J=6.3 Hz, 1H, NH), 9.31 (bs, 1H, NH); $^{13}$C NMR (acetone-d$_6$) δ 41.08 (CH$_2$), 124.88, 124.92, 125.13, 125.72, 126.12, 126.56, 128.07, 129.67, 129.80, 129.83, 133.08, 134.46, 168.34 (CO), 168.91 (CO).

Step c: General Procedure for Preparation of benzylidene-hydrazides

Aldehyde (1 mmol) was added to a stirred suspension of hydrazide 3a (1 mmol) in ethanol (10 mL) and refluxed for 1 hour. For compound C2.20, the resulting white solid was filtered and recrystallized from EtOH (50 mL). For compounds C2.11 and C2.05, the crude mixture was concentrated under vacuum and triturated in acetone.

N-(2-{(2E)-2-[(3-hydroxypyridin-2-yl)methylidene] hydrazinyl}-2-oxoethyl)naphthalene-1-carboxamide (C2.11)

Compound C2.11 was obtained as a yellow solid (237 mg, 64%) from 3-hydroxypyridine-2-carboxaldehyde. HPLC (Luna Phenyl-Hexyl column 75×4.6 mm, 3 μm) t$_r$ 4.84 min, purity 100%; IR (KBr)v 3485, 3119, 3031, 1702, 1644, 1601, 1580, 1544; $^1$H NMR (DMSO-d$_6$) (mixture of conformers) δ 4.12 and 4.47 (2d, J=5.5 Hz, 2H, CH$_2$), 7.34-7.49 (m, 2H, Ar), 7.59 (m, 3H, Ar), 7.70 (d, J=6.6 Hz, 1H, Ar), 7.99 (d, J=6.5 Hz, 1H, Ar), 8.04 (d, J=8.0 Hz, 1H, Ar), 8.21 (s, 1H, Ar), 8.35 and 8.45 (2s, 1H, CH=NH), 8.36 (d, J=7.9 Hz, 1H, Ar), 8.77 and 8.97 (2bt, 1H, NH) 10.30 and 11.50 (2s, 1H, OH), 11.76 and 12.22 (2s, 1H, NH); $^{13}$C NMR (DMSO-d$_6$) (mixture of conformers) δ 41.07, 42.15, 124.28, 124.56, 125.44, 125.79, 125.88, 125.98, 126.08, 126.16, 126.74, 127.12, 127.20, 128.62, 130.28, 130.37, 130.51, 133.59, 134.62, 134.98, 137.12, 138.26, 141.67, 144.82, 149.49, 154.02, 154.99, 166.32, 169.63, 169.71, 170.37; HRMS (ESI) m/z calcd for C$_{19}$H$_{17}$N$_4$O$_3$[M+H]$^+$: 349.1295. found: 349.1301.

N-{2-[(2E)-2-(2,6-dihydroxybenzylidene)hydrazinyl]-2-oxoethyl}naphthalene-1-carboxamide (C2.05)

Compound C2.05 was obtained as a white solid (181 mg, 50%) from 2,6-hydroxybenzaldehyde$^1$. HPLC (Luna Phenyl-Hexyl column 75×4.6 mm, 3 μm) t$_r$ 6.64 min, purity 99.7%; IR (KBr) v 3317, 3313, 3051, 1634, 1601, 1535; $^1$H NMR (DMSO-d$_6$) (mixture of conformers) δ 4.07 and 4.37 (2d, J=5.7 Hz, 2H, CH$_2$), 6.36-6.41 (m, 2H, Ar), 7.10 (t, J=8.2 Hz, 1H, Ar), 7.56-7.59 (m, 3H, Ar), 7.70 (d, J=6.5 Hz, 1H, Ar), 7.98 (d, J=5.9 Hz, 1H, Ar), 8.03 (d, J=8.2 Hz, 1H, Ar), 8.36 (m, 1H, Ar), 8.58 and 8.75 (2s, 1H, CH=N), 8.79 and 8.91 (2t, J=5.7 Hz, 1H, NH), 10.47 and 11.02 (2s, 2H, 2OH), 11.62 and 11.88 (2s, 1H, NH); $^{13}$C NMR (DMSO-d$_6$) (mixture of conformers) δ 41.62, 106.03, 106.12, 106.53, 106.66, 124.97, 125.32, 125.43, 125.67, 126.27, 126.66, 126.72, 128.15, 129.83, 129.92, 130.02, 132.23, 132.31, 133.13, 134.22, 134.51, 138.99, 143.42, 145.30, 157.98, 158.29, 165.17, 168.84, 169.19; HRMS (ESI) m/z calcd for C$_{20}$H$_{18}$N$_3$O$_4$ [M+H]$^+$: 364.1292. found: 364.1295.

N-{2-[(2E)-2-(4-fluoro-2-hydroxybenzylidene)hydrazinyl]-2-oxoethyl}naphthalene-1-carboxamide (C2.20)

Compound C2.20 was obtained as a white solid (264 mg, 72%) from 5-fluoro-2-hydroxybenzaldehyde. HPLC (Luna Phenyl-Hexyl column 75×4.6 mm, 3 μm) t$_r$ 6.94 min, purity 99.1%; IR (KBr) v 3264, 3062, 1685, 1636, 1541, 1282; $^1$H NMR (DMSO-d$_6$) (mixture of conformers) δ 4.09 and 4.49 (2d, J=5.8 Hz, 2H, CH$_2$), 6.92-6.96 (m, 1H, Ar), 7.08-7.15 (m, 1H, Ar), 7.45-7.59 (m, 4H, Ar), 7.69 (d, J=6.3 Hz, 1H, Ar), 7.98-8.04 (m, 2H, Ar), 8.32 and 8.45 (2s, 1H, CH=N), 8.36-8.42 (m, 1H, Ar), 8.75 and 8.93 (2t, J=5.8 Hz, 1H, NH), 10.09 and 10.88 (2s, 1H, OH), 11.57 and 11.93 (2s, 1H, NH); $^{13}$C NMR (DMSO-d$_6$) (mixture of conformers) δ 41.28, 42.15, 111.49, 111.73, 114.07, 114.30, 117.83, 117.91, 118.00, 118.07, 118.24, 118.30, 118.53, 120.23, 120.31, 121.82, 121.90, 125.46, 125.69, 125.82, 126.13, 126.21, 126.69, 126.72, 127.07, 127.16, 128.58, 130.30, 130.44, 133.59, 134.76, 135.18, 139.80, 145.41, 153.13, 153.91, 154.65, 154.94, 156.98, 157.27, 166.08, 169.60, 169.67, 170.65; HRMS (ESI) m/z calcd for C$_{20}$H$_{17}$FN$_3$O$_3$ [M+H]$^+$: 366.1250. found: 366.1248.

N-{2-[(2E)-2-(2-hydroxybenzylidene)hydrazinyl]-2-oxoethyl}naphthalene-1-carboxamide (compound 2)

Compound 2 was obtained starting with 2-hydroxybenzaldehyde giving a solid (g, %). The crude compound was purified by flash chromatography using EtOAc/hexanes as eluent to give pure compound 2 (g, %). IR (film); $^1$H NMR (CDCl$_3$); $^{13}$C NMR (CDCl$_3$); LRMS for C$_x$H$_y$ON [M+H]$^+$: m/z.

Procedures for the Preparation of 3-chlorobenzene-hydrazide Derivatives (Scheme Synthesis of Compound 3 and Derivatives)

Step a: Preparation of methyl-N-(3-chlorophenyl-1-ylcarbonyl)glycinate (6a)

Compound 6a was obtained using procedure described for preparation of amide 2a starting with methylglycinate hydrochloride (5 g, 39 mmol) and 3-chlorobenzoyl chloride reagent (5.6 mL, 44 mmol). The crude compound was purified by flash chromatography using DCM/EtOAc (98:2) as eluent to give pure compound 6a (4.1 g, 54%). $^1$H NMR (acetone-d$_6$) δ 3.70 (s, 3H, OMe), 4.15 (d, J=6 Hz, 2H, CH$_2$), 7.52 (t, J=7.8 Hz, 1H, Ar), 7.59 (d, J=8.0 Hz, 1H, Ar), 7.87 (d, J=7.7 Hz, 1H, Ar), 7.92 (s, 1H, Ar), 7.93 (bs, 1H, NH); $^{13}$C NMR (acetone-d$_6$) δ 41.99 (CH$_2$), 52.17 (OMe), 126.54, 128.15, 131.09, 132.17, 134.85, 137.07, 166.38 (CO), 170.10 (CO).

Step b: Preparation of N-(2-hydrazinyl-2-oxoethyl)-3-chlorophenyl-1-carboxamide (7a)

Following the procedure described for the preparation of naphthyl analog 3a, we obtained hydrazide 7a (2.6 g, 87%) from ester 6a (3 g, 12.5 mmol). $^1$H NMR (acetone-d$_6$) δ 3.84 (d, J=6.0 Hz, 2H, CH$_2$), 7.51 (t, J=7.8 Hz, 1H, Ar), 7.61 (d, J=8 Hz, 1H, Ar), 7.82 (d, J=7.7 Hz, 1H, Ar), 7.94 (s, 1H, Ar), 7.93 (t, J=5.8 Hz, 1H, NH), 9.16 (bs, 1H, NH); $^{13}$C NMR (acetone-d$_6$) δ 41.49 (CH$_2$), 125.96, 126.13, 127.10, 130.25, 131.10, 133.09, 136.08, 165.13 (CO), 168.08 (CO).

Step c: General Procedure for Preparation of benzylidene-hydrazides C3.1-2

Hydrazide 7a (1 mmol) was converted by condensation with aldehyde (1 mmol) into the corresponding derivatives C3.1-2 as described for the preparation of the naphthyl analogs C2-#.

3-chloro-N-(2-{2-[(E)-2-(2-hydroxy-3-methylphenyl)ethenyl]hydrazinyl}-2-oxoethyl)benzamide (C3-1)

Compound 3-1 was obtained as a white solid (338 mg, 76%) from 2-hydroxy-3-methylbenzaldehyde. HPLC (Luna Phenyl-Hexyl column 75×4.6 mm, 3 μm) t$_r$ 8.36 min, purity 100%; IR (KBr) v 3420, 3215, 3068, 1716, 1630, 1568, 1527; $^1$H NMR (DMSO-d$_6$) (mixture of conformers) δ 2.19 and 2.20 (2s, 3H, Me), 4.03 and 4.38 (2d, J=6.2 Hz, 2H, CH$_2$), 6.82-6.88 (m, 1H, Ar), 7.20 (d, J=7.9 Hz, 1H, Ar), 7.27 and 7.34 (d, J=7.4 Hz, 1H, Ar), 7.55 (t, J=7.9 Hz, 1H, Ar), 7.65 (d, J=8 Hz, 1H, Ar), 7.87 (d, J=7.8 Hz, Ar), 7.97 (s, 1H, Ar), 8.24 and 8.39 (s, 1H, CH=N), 8.93 and 9.10 (t, J=5.6 Hz, 1H, NH), 10.16 and 11.72 (2s, 1H, OH), 11.64 and 11.86 (2s, 1H, NH); $^{13}$C NMR (DMSO-d$_6$) (mixture of conformers) δ 15.89, 16.12, 40.37, 117.55, 118.74, 119.34, 119.96, 125.41, 125.56, 126.53, 126.61, 127.63, 127.73, 129.11, 130.85, 131.78, 132.86, 133.69, 136.21, 136.41, 146.08, 149.78, 155.32, 156.31, 165.80, 169.63; HRMS (ESI) m/z calcd for C$_{17}$H$_{17}$ClN$_3$O$_3$[M+H]$^+$: 346.0953. found: 346.0954.

3-chloro-N-(2-{2-[(E)-2-(1-hydroxynaphthalen-2-yl)ethenyl]hydrazinyl}-2-oxoethyl)benzamide (C3-2)

Compound C$_{3-2}$ was obtained as a yellow solid (327 mg, 82%) from 1-hydroxy-2-naphthaldehyde. HPLC (Luna Phenyl-Hexyl column 75×4.6 mm, 3 μm) t$_r$ 10.81 min, purity 99.9%; IR (KBr)v 3260, 3064, 1675, 1634, 1564, 1537; $^1$H NMR (DMSO-d$_6$) (mixture of conformers) δ 4.06 and 4.47 (2d, J=5.7 Hz, 2H, CH$_2$), 7.44-7.68 (m, 6H, Ar), 7.88 (t, J=6.80 Hz, 2H, Ar), 7.98 (s, 1H, Ar), 8.28 (d, J=8.0 Hz, 1H) 8.46 and 8.55 (s, 1H, CH=N), 8.95 and 9.12 (t, J=5.6 Hz, 1H, NH), 10.80 and 12.71 (2s, 1H, OH), 11.68 and 11.96 (2s, 1H, NH); $^{13}$C NMR (DMSO-d$_6$) (mixture of conformers) δ 41.18, 42.44, 111.79, 114.08, 119.24, 120.15, 122.88, 123.05, 124.75, 125.20, 125.48, 126.16, 126.24, 126.54, 126.63, 127.15, 127.63, 127.73, 128.02, 128.11, 128.21, 128.42, 130.89, 131.72, 131.80, 133.69, 134.93, 135.08, 136.24, 136.46, 144.85, 149.64, 153.63, 155.24, 165.73, 165.81, 169.79; HRMS (ESI) m/z calcd for C$_{20}$H$_{17}$ClN$_3$O$_3$[M+H]$^+$: 382.0956. found: 382.0953.

3-chloro-N-(2-{(2E)-2-[2-hydroxy-3-(prop-2-en-1-yl)benzylidene]hydrazinyl}-2-oxoethyl)benzamide (compound 3)

Compound 3 was obtained starting with 2-hydroxy-3-(prop-2-en-1yl)benzaldehyde. The crude compound was purified by flash chromatography using EtOAc/hexanes as eluent to give pure compound 3 (g, %). IR (film); $^1$H NMR (CDCl$_3$); $^{13}$C NMR (CDCl$_3$); LRMS for C$_x$H$_y$ON [M+H]$^+$: m/z.

The present description refers to a number of documents, the content of which is herein incorporated by reference in their entirety.

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

REFERENCES

1. Gilbert C, Bestman-Smith J and Boivin G. Resistance of herpesvirus to antiviral drugs: clinical impacts and molecular mechanisms. Drug Resist Updat. 2002 April; 5(2):88-114.
2. Boivin G, Gilbert C, Gaudreau A et al. Rate of emergence of cytomegalovirus (CMV) mutations in leukocytes of patients with acquired immunodeficiency syndrome who are receiving valganciclovir as induction and maintenance therapy for CMV retinitis. J Infect Dis. 2001 Dec. 15; 184(12):1598-602.
3. Limaye A P, Corey L and Koelle D M et al. Emergence of ganciclovir-resistant cytomegalovirus disease among recipients of solid-organ transplants. Lancet. 2000 Aug. 19; 356(9230):645-9.
4. Jabs D A, Enger C, Forman M et al. Incidence of foscarnet resistance and cidofovir resistance in patients treated for cytomegalovirus retinitis. The Cytomegalovirus Retinitis and Viral Resistance Study Group. Antimicrob Agents Chemother. 1998 September; 42(9):2240-4.
5. Weinberg A, Jabs D A, Chou S et al. Mutations conferring foscarnet resistance in a cohort of patients with acquired immunodeficiency syndrome and cytomegalovirus retinitis. J Infect Dis. 2003 Mar. 1; 187(5):777-84.
6. Cihlar T, Fuller M D, Mulato A S et al. A point mutation in the human cytomegalovirus DNA polymerase gene selected in vitro by cidofovir confers a slow replication phenotype in cell culture. Virology. 1998 Sep. 1; 248(2): 382-93.
7. Chou S, Lurain N S, Thompson K D et al. Viral DNA polymerase mutations associated with drug resistance in human cytomegalovirus. J Infect Dis. 2003 Jul. 1; 188(1): 32-9.
8. Shi R, Azzi A, Gilbert C et al. Three-dimensional modeling of cytomegalovirus DNA polymerase and preliminary analysis of drug resistance. Proteins. 2006 Aug. 1; 64(2): 301-7.
9. Liu S, Knafels J D, Chang J S et al. Crystal structure of the herpes simplex virus 1 DNA polymerase. J Biol. Chem. 2006 Jun. 30; 281(26):18193-200.
10. Jones G, Willett P and Glen R C. Molecular recognition of receptor sites using a genetic algorithm with a description of desolvation J. Mol. Biol. 1995; 245:43-53.
11. Eldridge M D, Murray C D, Auton T R et al. Empirical scoring functions: I. The development of a fast empirical scoring function to estimate the binding affinity of ligands in receptor complexes. Journal of Computer-Aided Molecular Design 1997; 11:425-445.
12. Irwin and Shoichet. ZINC—a free database of commercially available compounds for virtual screening. J. Chem. Inf. Model. 2005; 45(1):177-82.

13. Lipinski A, Lombardo F, Dominy B W et al. Experimental and computational approaches to estimate solubility and permeability in drug discovery and development settings. Adv Drug Del Rev. 1997; 23:3-25.
14. Schmit I and Boivin G. Characterization of the DNA polymerase and thymidine kinase genes of herpes simplex virus isolates from AIDS patients in whom acyclovir and foscarnet therapy sequentially failed. J Infect Dis. 1999 August; 180(2):487-90.
15. McSharry J J, Lurain N S, Drusano G L et al. Rapid ganciclovir susceptibility assay using flow cytometry for human cytomegalovirus clinical isolates. Antimicrob Agents Chemother. 1998 September; 42(9):2326-31.
16. Talarico C L, Burnette T C, Miller W H et al. Acyclovir is phosphorylated by the human cytomegalovirus UL97 protein. Antimicrob Agents Chemother. 1999 August; 43(8):1941-6.
17. Landry M L, Stanat S, Biron K et al. A standardized plaque reduction assay for determination of drug susceptibilities of cytomegalovirus clinical isolates. Antimicrob Agents Chemother. 2000 March; 44(3):688-92.
18. Avdeef A, Strafford M, Block E et al. Drug absorption in vitro model: filter-immobilized artificial membranes. 2. Studies of the permeability properties of lactones in Piper methysticum Forst. Eur J Pharm Sci 2001; 14:271-80.

The invention claimed is:

1. A pharmaceutical composition comprising a compound of formula IA or formula IB or a pharmaceutically acceptable salt thereof and a pharmaceutically acceptable carrier:

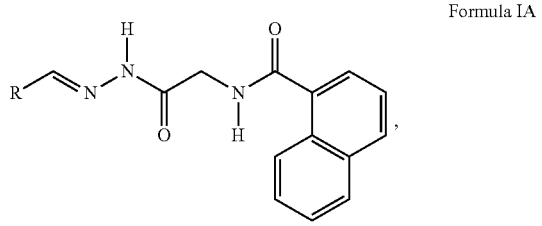

Formula IA

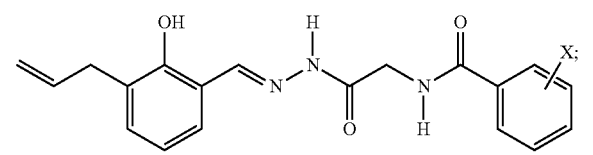

Formula IB wherein R is selected from the group consisting of unsubstituted phenyl or a substituted phenyl of formula II:

II an unsubstituted pyridine or a substituted pyridine selected from the group consisting of:

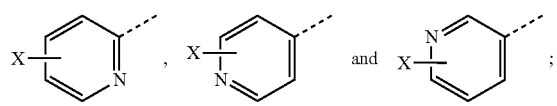

a pyrimidine selected from the group consisting of:

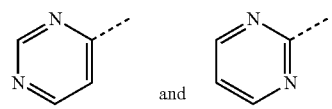

wherein X and Y each are independently selected from the group consisting of H, —OR$_1$, NH$_2$, F, Cl, Br, I, an alkyl group of 1 to 3 carbon atoms and an allyl group;

and wherein R$_1$ is selected from the group consisting of H and an alkyl group of 1 to 3 carbon atoms, provided that said compound of formula IA is not

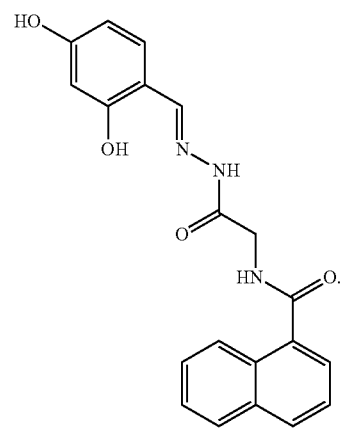 [SMILES: O=C(CNC(=O)c1cccc2ccccc12)N/N=C/c1ccc(O)cc1O]

2. The pharmaceutical composition of claim 1, wherein X is OH and Y is F.

3. The pharmaceutical composition of claim 1, wherein X is OH and Y is H.

4. The pharmaceutical composition of claim 1, wherein R is selected from the group consisting of:

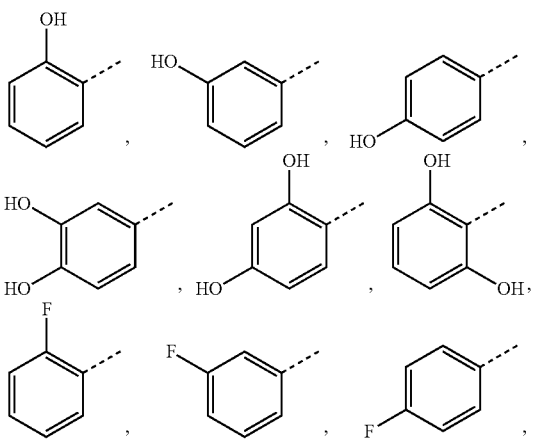

-continued

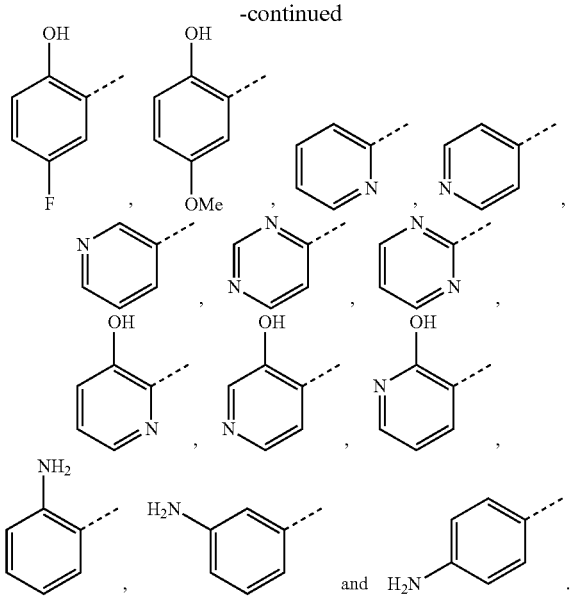

5. A pharmaceutical composition comprising:
a. a compound selected from the group consisting of:
   i. N-(2-(2-(2-hydroxy-5-methoxybenzylidene)hydrazino)-2-oxoethyl)-3-methyl-benzamide;
   ii. N-(2-(2-(2-hydroxybenzylidene)hydrazino)-2-oxoethyl)-1-naphthamide;
   iii. N-(2-(2-(3-allyl-2-hydroxybenzylidene)hydrazino)-2-oxoethyl)-3-chlorobenzamide;
   iv. N-[2-(4-methoxyphenyl)ethyl]-2-[(1-phenyl-1H-tetrazol-5-yl)thio]acetamide;
   v. 1-(2-chloro-5-nitrophenyliminomethyl)-2-naphthol;
   vi. N-1H-tetrazol-5-yl-4-biphenylcarboxamide;
   vii. 9-anthracenecarbaldehyde 1H-tetrazol-5-ylhydrazone;
   viii. N-{[(2-methyl-2H-tetrazol-5-yl)amino]carbonothioyl}-2-thiophenecarboxamide;
   ix. N-(2-(2-(2-hydroxy-5-methoxybenzylidene)hydrazino)-2-oxoethyl)-1-naphthamide;
   x. N-(2-(2-(3-allyl-2-hydroxybenzylidene)hydrazino)-2-oxoethyl)-2-chlorobenzamide;
   xi. N-(2-(2-(3-allyl-2-hydroxybenzylidene)hydrazino)-2-oxoethyl)-4-chlorobenzamide;
   xii. N-(2-(2-(3-allyl-2-hydroxybenzylidene)hydrazino)-2-oxoethyl)-1-naphthamide;
   xiii. (E)-N-(2-(2-(3-hydroxybenzylidene)hydrazinyl)-2-oxoethyl)-1-naphthamide;
   xiv. (E)-N-(2-(2-(4-hydroxybenzylidene)hydrazinyl)-2-oxoethyl)-1-naphthamide;
   xv. (E)-N-(2-(2-(3,4-dihydroxybenzylidene)hydrazinyl)-2-oxoethyl)-1-naphthamide;
   xvi. (E)-N-(2-(2-(2,6-dihydroxybenzylidene)hydrazinyl)-2-oxoethyl)-1-naphthamide;
   xvii. (E)-N-(2-oxo-2-(2-(pyrimidin-4-ylmethylene)hydrazinyl)ethyl)-1-naphthamide;
   xviii. (E)-N-(2-oxo-2-(2-(pyridin-2-ylmethylene)hydrazinyl)ethyl)-1-naphthamide;
   xix. (E)-N-(2-oxo-2-(2-(pyridin-4-ylmethylene)hydrazinyl)ethyl)-1-naphthamide;
   xx. (E)-N-(2-oxo-2-(2-(pyridin-3-ylmethylene)hydrazinyl)ethyl)-1-naphthamide;
   xxi. (E)-N-(2-oxo-2-(2-(pyrimidin-2-ylmethylene)hydrazinyl)ethyl)-1-naphthamide;
   xxii. (E)-N-(2-(2-((3-hydroxypyridin-2-yl)methylene)hydrazinyl)-2-oxoethyl)-1-naphthamide;
   xxiii. (E)-N-(2-(2-((3-hydroxypyridin-4-yl)methylene)hydrazinyl)-2-oxoethyl)-1-naphthamide;
   xxiv. (E)-N-(2-(2-((2-hydroxypyridin-3-yl)methylene)hydrazinyl)-2-oxoethyl)-1-naphthamide;
   xxv. (E)-N-(2-(2-(2-aminobenzylidene)hydrazinyl)-2-oxoethyl)-1-naphthamide;
   xxvi. (E)-N-(2-(2-(3-aminobenzylidene)hydrazinyl)-2-oxoethyl)-1-naphthamide;
   xxvii. (E)-N-(2-(2-(4-aminobenzylidene)hydrazinyl)-2-oxoethyl)-1-naphthamide;
   xxviii. (E)-N-(2-(2-(2-fluorobenzylidene)hydrazinyl)-2-oxoethyl)-1-naphthamide;
   xxix. (E)-N-(2-(2-(3-fluorobenzylidene)hydrazinyl)-2-oxoethyl)-1-naphthamide;
   xxx. (E)-N-(2-(2-(4-fluorobenzylidene)hydrazinyl)-2-oxoethyl)-1-naphthamide, and;
   xxxi. (E)-N-(2-(2-(5-fluoro-2-hydroxybenzylidene)hydrazinyl)-2-oxoethyl)-1-naphthamide; and
b. a pharmaceutically acceptable carrier.

6. The pharmaceutical composition of claim 1, wherein said composition interferes with herpesvirus replication.

7. A compound of formula IA or a pharmaceutically acceptable salt thereof:

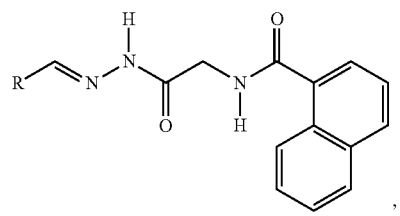

Formula IA wherein R is selected from the group consisting of unsubstituted phenyl or a substituted phenyl of formula II:

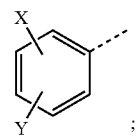

II an unsubstituted pyridine or a substituted pyridine selected from the group consisting of:

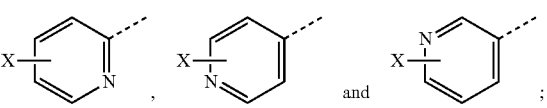

and
a pyrimidine selected from the group consisting of:

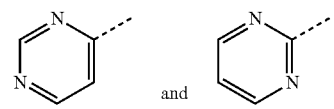

wherein X and Y each are independently selected from the group consisting of H, —OR₁, NH₂, F, Cl, Br, I, an alkyl group of 1 to 3 carbon atoms and an allyl group;
and wherein R₁ is selected from the group consisting of H and an alkyl group of 1 to 3 carbon atoms provided that the compound is not:
i. N-(2-(2-(2-hydroxybenzylidene)hydrazino)-2-oxoethyl)-1-naphthamide;
ii. N-(2-(2-(2-hydroxy-5-methoxybenzylidene)hydrazino)-2-oxoethyl)-1-naphthamide;
iii. N-(2-(2-(3-allyl-2-hydroxybenzylidene)hydrazino)-2-oxoethyl)-3-chlorobenzamide; or
iv.

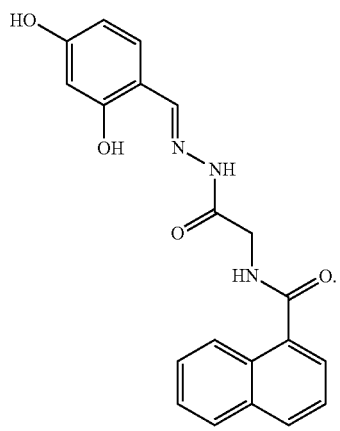 [SMILES: O=C(CNC(=O)c1cccc2ccccc12)N/N=C/c1ccc(O)cc1O]

8. The compound of claim 7, wherein X is OH and Y is F.
9. The compound of claim 7, wherein X is OH and Y is OH.
10. The compound of claim 7, wherein R is a substituted pyridine of formula

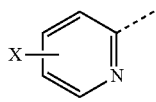

and wherein X is OH.

11. A method of treating a herpesvirus infection, the method comprising administering a compound of formula IA or formula IB to a mammal in need:

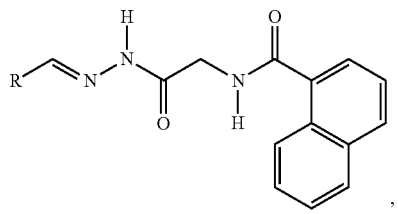

Formula IA

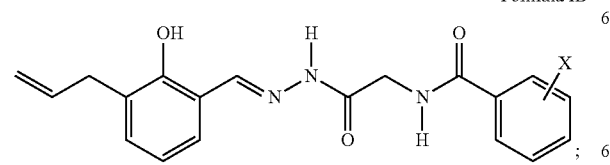

Formula IB wherein R is selected from the group consisting of unsubstituted phenyl or a substituted phenyl of formula II:

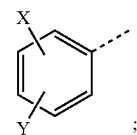

II an unsubstituted pyridine or a substituted pyridine selected from the group consisting of:

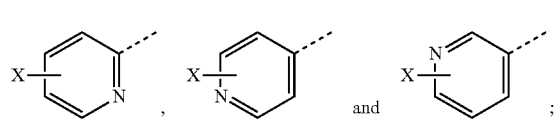

and a pyrimidine selected from the group consisting of:

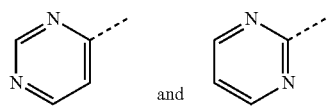

wherein X and Y each are independently selected from the group consisting of H, —OR₁, NH₂, F, Cl, Br, I, an alkyl group of 1 to 3 carbon atoms and an allyl group;
and wherein R₁ is selected from the group consisting of H and an alkyl group of 1 to 3 carbon atoms.

12. The method of claim 11, wherein R is selected from the group consisting of unsubstituted phenyl or a substituted phenyl of formula II:

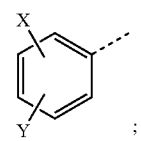

II and
an unsubstituted pyridine or a substituted pyridine of formula:

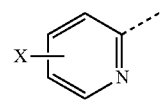

wherein X and Y each are independently selected from the group consisting of H, —OR₁, NH₂, F, Cl, Br, I, an alkyl group of 1 to 3 carbon atoms and an allyl group;
and wherein R₁ is selected from the group consisting of H and an alkyl group of 1 to 3 carbon atoms.

13. The method of claim 12, wherein R is a substituted phenyl of formula II and wherein X is OR₁ and Y is F, OR₁ or H.

14. The method of claim 13, wherein X is OH and Y is F.
15. The method of claim 13, wherein X is OH and Y is H.

16. The method of claim 13, wherein X is OR$_1$ and Y is OH.
17. The method of claim 16, wherein R$_1$ is H.
18. The method of claim 16, wherein R$_1$ is methyl.
19. The method of claim 12, wherein R is a substituted pyridine of formula

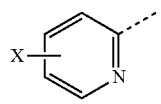

and wherein X is OR$_1$.
20. The method of claim 19, wherein R$_1$ is H.
21. The method of claim 11, wherein R is

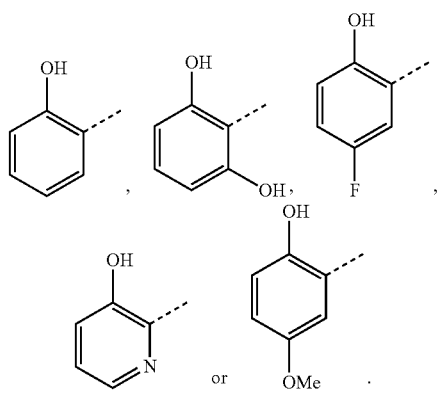

22. The method of claim 11, wherein the mammal in need is an immunocompromised individual suffering from HIV-infection or neoplasia.
23. The method of claim 11, wherein the mammal in need is a transplant recipient.
24. The method of claim 11, wherein the mammal in need suffers from chickenpox or shingles associated with varicella zoster virus.
25. The method of claim 11, wherein the mammal in need has an oro-labial or genital infection associated with HSV-1 or HSV-2.
26. The method of claim 11, wherein the mammal in need suffers from pneumonitis, colitis or retinitis associated with cytomegalovirus.
27. The method of claim 11, wherein the herpesvirus is characterized as being resistant to a pyrophosphate analogue, a nucleoside analogue or to a prodrug or derivative thereof.
28. The method of claim 11, provided that said compound of formula IA is not

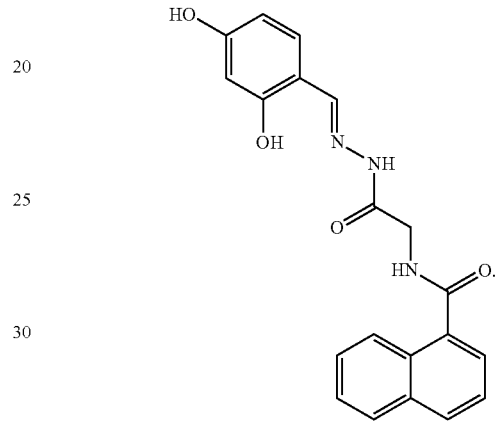

* * * * *